US012767713B2

(12) United States Patent
Ding et al.

(10) Patent No.: US 12,767,713 B2
(45) Date of Patent: Oct. 20, 2026

(54) ANTI-SIGLEC15 ANTIBODY AND USE THEREOF

(71) Applicant: CSPC MEGALITH BIOPHARMACEUTICAL CO., LTD., Shijiazhuang (CN)

(72) Inventors: Huandi Ding, Shijiazhuang (CN); Xiwu Hui, Shijiazhuang (CN); Bing Yao, Shijiazhuang (CN); Boning Liu, Shijiazhuang (CN); Yancui Wang, Shijiazhuang (CN); Wenbin Li, Shijiazhuang (CN); Ruya Zou, Shijiazhuang (CN); Qing Sun, Shijiazhuang (CN); Can Yuan, Shijiazhuang (CN)

(73) Assignee: CSPC MEGALITH BIOPHARMACEUTICAL CO., LTD., Shijiazhuang (CN)

( * ) Notice: Subject to any disclaimer, the term of this patent is extended or adjusted under 35 U.S.C. 154(b) by 649 days.

(21) Appl. No.: 18/278,014

(22) PCT Filed: Feb. 21, 2022

(86) PCT No.: PCT/CN2022/077030
§ 371 (c)(1),
(2) Date: Aug. 21, 2023

(87) PCT Pub. No.: WO2022/179466
PCT Pub. Date: Sep. 1, 2022

(65) Prior Publication Data

US 2025/0326838 A1 Oct. 23, 2025

(30) Foreign Application Priority Data

Feb. 25, 2021 (CN) ........................ 202110211997.5

(51) Int. Cl.

| | |
|---|---|
| ***A61K 39/395*** | (2006.01) |
| ***A61K 47/68*** | (2017.01) |
| ***A61P 35/00*** | (2006.01) |
| ***A61P 37/06*** | (2006.01) |
| ***C07K 16/28*** | (2006.01) |

(52) U.S. Cl.
CPC ...... *C07K 16/2803* (2013.01); *A61K 39/3955* (2013.01); *A61K 47/6849* (2017.08); *A61P 35/00* (2018.01); *A61P 37/06* (2018.01); *C07K 16/28* (2013.01); *C07K 16/2818* (2013.01); *C07K 16/2827* (2013.01); *C07K 2317/24* (2013.01); *C07K 2317/52* (2013.01); *C07K 2317/565* (2013.01); *C07K 2317/92* (2013.01)

(58) Field of Classification Search
CPC ............................ A61K 39/3955; C07K 16/28
See application file for complete search history.

(56) References Cited

U.S. PATENT DOCUMENTS

| | | | | |
|---|---|---|---|---|
| 2015/0037356 A1* | 2/2015 | Elvin | ...................... A61P 35/02 | 435/69.6 |
| 2019/0202912 A1* | 7/2019 | Liu | .................... C07K 16/2803 | |

FOREIGN PATENT DOCUMENTS

| | | | |
|---|---|---|---|
| CA | 2698326 | A1 | 4/2009 |
| CN | 102803293 | A | 11/2012 |
| CN | 104321430 | A | 1/2015 |
| CN | 104507969 | A | 4/2015 |
| CN | 110035769 | A | 7/2019 |
| JP | 2015524256 | A | 8/2015 |
| WO | 2011041894 | A1 | 4/2011 |
| WO | 2017083354 | A1 | 5/2017 |
| WO | 2018057735 | A1 | 3/2018 |

OTHER PUBLICATIONS

International Search Report and Written Opinion mailed on May 12, 2022, received for PCT Application PCT/CN2022/077030, filed on Feb. 21, 2022, 17 pages including English Translation.
Notice of Reasons for Refusal mailed Sep. 10, 2024, in Japanese Application No. 2023-552073, 12 pages. (With English translation).
Supplementary European Search Report mailed Jul. 22, 2024, in European Application No. 22758830.8, 12 pages.

* cited by examiner

*Primary Examiner* — Xiaozhen Xie
(74) *Attorney, Agent, or Firm* — XSENSUS LLP

(57) ABSTRACT

Provided in the present application is an anti-Siglec 15 antibody or an antigen-binding fragment thereof, a pharmaceutical composition and immunoconjugate comprising the antibody or antigen-binding fragment, a nucleic acid molecule encoding the antibody or antigen-binding fragment thereof, a vector comprising the nucleic acid molecule, a host cell comprising the vector, a method for preparing the antibody or antigen-binding fragment, and the biological medical use of the antibody or antigen-binding fragment. The use comprises regulating the immune response, reversing the inhibition of the Siglec15 protein on PBMC lymphocyte proliferation or treating tumors associated with abnormal Siglec 15 expression.

15 Claims, 4 Drawing Sheets

Specification includes a Sequence Listing.

ANTI-SIGLEC15 ANTIBODY AND USE THEREOF

REFERENCES TO RELATED APPLICATIONS

This application is a National Stage Application under 35 U.S.C. 371 based on International Application No. PCT/CN2022/077030, filed on Feb. 21, 2022, which claims the priority of Chinese Patent Application No. 202110211997.5, filed on Feb. 25, 2021, the entire contents of each are hereby incorporated by reference for all purposes.

SEQUENCE LISTING

The instant application contains a Sequence Listing which has been submitted electronically in ASCII format and is hereby incorporated by reference in its entirety. Said ASCII copy, created on Mar. 20, 2024, is named 22535US01_SL.txt and is 32 KB in size.

TECHNICAL FIELD

The present application generally relates to the field of biopharmaceuticals, in particular, to a novel anti-Siglec15 antibody or antigen-binding fragment thereof, a pharmaceutical composition comprising the antibody or antigen-binding fragment thereof, and a pharmaceutical use of the antibody or antigen-binding fragment thereof.

BACKGROUND OF THE ART

Sialic acid-binding immunoglobulin-type lectin (Siglec) is a member of the immunoglobulin superfamily and belongs to type I transmembrane glycoprotein. Its molecular structure consists of three parts: an extracellular domain, a transmembrane domain and an intracellular domain. Studies have shown that members of the Siglec family play an important role in the activation and proliferation of immune cells and in mediating physiological and pathological processes. At the same time, members of the Siglec family are also involved in the regulation of immune tolerance, and play an important role in immune regulation in autoimmune diseases, inflammatory responses and tumorigenesis.

Siglec15 is a member of the Siglec family, consisting of 328 amino acid residues, and its extracellular domain (ECD) contains an immunoglobulin variable domain (Ig-like V-type Domain, IgV) and a type 2 constant domain (Ig-like C2-type Domain, IgC2), wherein the IgV domain is a key site for binding of Siglec15 and Siglec15 ligand (e.g. glycoprotein with Neu5Acα2-6GalNAcα-structure, myelin-associated glycoprotein (MAG), Leucine Rich Repeat Containing Protein 4C (LRRC4C) or Siglec15-counter receptor). It is shown from protein sequence analysis that Siglec15 has more than 30% homology with the B7 gene family of T cells in terms of structure. Siglec15 is originally found to play an important role in physiological bone reorganization, and is also involved in pathological bone loss caused by estrogen deficiency. Recent studies have shown that Siglec15 is a negative regulator of tumor immunity and plays a role in tumor immunity. Siglec15 is highly expressed in many types of cancer cells and tumor-associated macrophages, and it binds to unknown receptors on T cells, leading to the inhibition of T cell function. And it can regulate immunosuppression in a manner independent of the B7-H1 (PD-L1)/PD-1 pathway. At the same time, blocking the immunosuppressive effect of Siglec15 can restore or improve the body's anti-tumor immune response.

Currently, the anti-Siglec15 antibody drug used for the treatment of a solid tumor is only NC-318 from NextCure, which is in a clinical trial, and its epitope is still unclear. Based on the fact that there are currently no marketed drugs for the Siglec 15 target and there are not many clinical projects currently underway, there is an urgent need to provide patients with more Siglec15 antibody drugs with better therapeutic effects.

SUMMARY OF THE INVENTION

In a first aspect, the present application provides an anti-Siglec15 antibody or antigen-binding fragment thereof which comprises a heavy chain variable region and a light chain variable region, wherein the heavy chain variable region comprises a heavy chain CDR1 (HCDR1), a heavy chain CDR2 (HCDR2) and heavy chain CDR3 (HCDR3), and the light chain variable region comprises light chain CDR1 (LCDR1), light chain CDR2 (LCDR2) and light chain CDR3 (LCDR3), wherein:

the heavy chain variable region comprises HCDR1 having the amino acid sequence set forth in SEQ ID NO: 6, HCDR2 having the amino acid sequence set forth in SEQ ID NO: 7 and HCDR3 having the amino acid sequence set forth in SEQ ID NO: 8, and the light chain variable region comprises LCDR1 having the amino acid sequence set forth in SEQ ID NO: 9, LCDR2 having the amino acid sequence set forth in SEQ ID NO: 10 and LCDR3 having the amino acid sequence set forth in SEQ ID NO: 11; or the heavy chain variable region comprises HCDR1 having the amino acid sequence set forth in SEQ ID NO: 6, HCDR2 having the amino acid sequence set forth in SEQ ID NO: 12 and HCDR3 having the amino acid sequence set forth in SEQ ID NO: 8, and the light chain variable region comprises LCDR1 having the amino acid sequence set forth in SEQ ID NO: 13, LCDR2 having the amino acid sequence set forth in SEQ ID NO: 10 and LCDR3 having the amino acid sequence set forth in SEQ ID NO: 11; or the heavy chain variable region comprises HCDR1 having the amino acid sequence set forth in SEQ ID NO: 14, and HCDR2 having the amino acid sequence set forth in SEQ ID NO: 15 and HCDR3 having the amino acid sequence set forth in SEQ ID NO: 16, and the light chain variable region comprises LCDR1 having the amino acid sequence set forth in SEQ ID NO: 17, LCDR2 having the amino acid sequence set forth in SEQ ID NO: 18 and LCDR3 having the amino acid sequence set forth in SEQ ID NO: 19; or the heavy chain variable region comprises HCDR1 having the amino acid sequence set forth in SEQ ID NO: 20, HCDR2 having the amino acid sequence set forth in SEQ ID NO: 21 and HCDR3 having the amino acid sequence set forth in SEQ ID NO: 22, and the light chain variable region comprises LCDR1 having the amino acid sequence set forth in SEQ ID NO: 23, LCDR2 having the amino acid sequence set forth in SEQ ID NO: 24 and LCDR3 having the amino acid sequence set forth in SEQ ID NO: 25, wherein the amino acid sequences of HCDR1, HCDR2, HCDR3 and LCDR1, LCDR2, LCDR3 are defined according to Kabat.

In a second aspect, the present application provides an anti-Siglec15 antibody or antigen-binding fragment thereof that specifically binds to a polypeptide having the amino acid sequence described in any one of (a) to (e):

(a) the amino acid sequence set forth in SEQ ID NO: 1;

(b) the amino acid sequence consisting of amino acid residues at positions 20 to 328 in the amino acid sequence set forth in SEQ ID NO: 1;

(c) the amino acid sequence consisting of amino acid residues at positions 1 to 263 in the amino acid sequence set forth in SEQ ID NO: 1;

(d) the amino acid sequence consisting of amino acid residues at positions 20 to 263 in the amino acid sequence set forth in SEQ ID NO: 1;

(e) the amino acid sequence having substitution, deletion or addition of one or more amino acid residues in the amino acid sequences described in (a) to (d).

In a third aspect, the present application provides an anti-Siglec15 antibody or antigen-binding fragment thereof that comprises a heavy chain variable region and a light chain variable region, wherein the heavy chain variable region has the amino acid sequence having at least 80%, at least 90%, at least 95%, or at least 99% homology with the amino acid sequence set forth in SEQ ID NO: 26, 28, 30 or 32, and the light chain variable region has the amino acid sequence having at least 80%, at least 90%, at least 95%, or at least 99% homology with the amino acid sequence set forth in SEQ ID NO: 27, 29, 31 or 33.

In a fourth aspect, the present application provides an anti-Siglec15 antibody or antigen-binding fragment thereof that comprises a heavy chain variable region and a light chain variable region, wherein the heavy chain variable region comprises a heavy chain CDR1 (HCDR1), a heavy chain CDR2 (HCDR2) and heavy chain CDR3 (HCDR3), wherein the heavy chain variable region comprises HCDR1 having the amino acid sequence set forth in SEQ ID NO: 6, HCDR2 having the amino acid sequence set forth in SEQ ID NO: 7 and HCDR3 having the amino acid sequence set forth in SEQ ID NO: 8; or the heavy chain variable region comprises HCDR1 having the amino acid sequence set forth in SEQ ID NO: 6, HCDR2 having the amino acid sequence set forth in SEQ ID NO: 12 and HCDR3 having the amino acid sequence set forth in SEQ ID NO: 8; or the heavy chain variable region comprises HCDR1 having the amino acid sequence set forth in SEQ ID NO: 14, HCDR2 having the amino acid sequence set forth in SEQ ID NO: 15, and HCDR3 having the amino acid sequence set forth in SEQ ID NO: 16; or the heavy chain variable region comprises HCDR1 having the amino acid sequence set forth in SEQ ID NO: 20 HCDR2 having the amino acid sequence set forth in SEQ ID NO: 21 and HCDR3 having the amino acid sequence set forth in SEQ ID NO: 22, wherein the amino acid sequences of HCDR1, HCDR2, and HCDR3 are defined according to Kabat.

In a fifth aspect, the present application provides an immunoconjugate comprising the anti-Siglec15 antibody or antigen-binding fragment thereof described in the first to fourth aspects conjugated to a therapeutic agent.

In a sixth aspect, the present application provides a pharmaceutical composition comprising the anti-Siglec15 antibody or antigen-binding fragment thereof described in the first to fourth aspects or the immunoconjugate described in the fifth aspect, and a pharmaceutically acceptable excipient, diluent agent or carrier.

Further, the present application provides a use of the anti-Siglec15 antibody or antigen-binding fragment thereof described in the first to fourth aspects or the immunoconjugate described in the fifth aspect or the pharmaceutical composition described in the sixth aspect in regulating the immune response in an individual, reversing the inhibition of Siglec15 protein on the proliferation of PBMC lymphocytes, reversing the inhibition of Siglec15 protein on the secretion of IFN-γ from PBMC lymphocytes, and inhibiting growth of tumor cells in an individual or treating a hyperproliferative disease (for example, a hyperproliferative disease associated with aberrant expression of Siglec15).

In a seventh aspect, the present application provides a use of the anti-Siglec 15 antibody or antigen-binding fragment thereof described in the first to fourth aspects or the immunoconjugate described in the fifth aspect or the pharmaceutical composition described in the sixth aspect in the preparing a medicament for regulating the immune response in an individual, reversing the inhibition of Siglec15 protein on the proliferation of PBMC lymphocytes, reversing the inhibition of Siglec15 protein on the secretion of IFN-γ from PBMC lymphocytes, and inhibiting growth of tumor cells in an individual or treating a hyperproliferative disease (for example, a hyperproliferative disease associated with aberrant expression of Siglec15).

In an eighth aspect, the present application provides a method for regulating the immune response in an individual, reversing the inhibition of Siglec15 protein on the proliferation of PBMC lymphocytes, reversing the inhibition of Siglec15 protein on the secretion of IFN-γ from PBMC lymphocytes, and inhibiting growth of tumor cells in an individual or treating a hyperproliferative disease (for example, a hyperproliferative disease associated with aberrant expression of Siglec15), comprising administering to an individual in need a therapeutically effective amount of the anti-Siglec 15 antibody or antigen-binding fragment thereof described in the first to fourth aspects or the immunoconjugate described in the fifth aspect or the pharmaceutical composition described in the sixth aspect.

In a ninth aspect, the present application provides an isolated polynucleotide encoding the anti-Siglec15 antibody or antigen-binding fragment described in the first to fourth aspects.

In a tenth aspect, the present application provides a vector comprising a polynucleotide encoding the anti-Siglec 15 antibody or antigen-binding fragment described in the first to fourth aspects.

In an eleventh aspect, the present application provides an isolated host cell comprising the vector described in the tenth aspect.

In a twelfth aspect, the present application provides a method for preparing the anti-Siglec 15 antibody or antigen-binding fragment thereof described in the first to fourth aspects, comprising a step of culturing the host cell described in the eleventh aspect. In some embodiments of the twelfth aspect, the method further comprises the step of isolating the anti-Siglec15 antibody or antigen-binding fragment thereof.

DETAILED DESCRIPTION OF EXEMPLARY EMBODIMENTS

Figure 1:
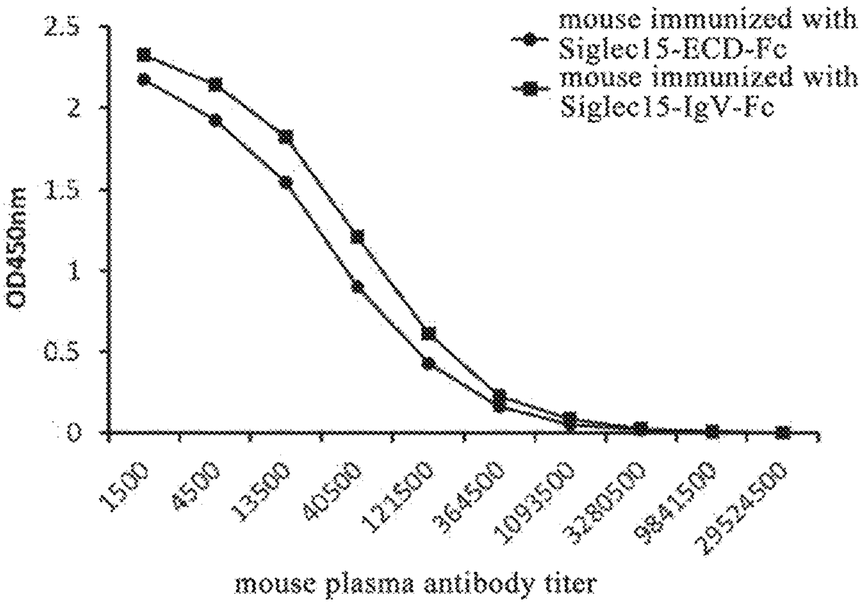
FIG. 1 shows the plasma antibody titer curves of mice immunized with Siglec15-ECD-Fc and Siglec 15-IgV-Fc proteins.

Based on the molecular signal transduction mechanism of Siglec15, the inventors of the present application designed an antibody screening strategy, and finally screened out a variety of anti-Siglec15 antibodies exhibiting excellent characteristics, for example, compared with the control antibody, the anti-Siglec15 antibody of the present application has a higher affinity with human Siglec15 and can restore Siglec15-mediated inhibition of T cell activity to a greater extent. In addition, the anti-Siglec15 antibody of the present application shows the property of modulating the immune response.

Definition

Unless defined otherwise, all technical and scientific terms used herein have the common meaning as commonly understood by one of ordinary skill in the art. For definitions and terms in this field, professionals can specifically refer to Current Protocols in Molecular Biology (Ausubel). Abbreviations for amino acid residues are the standard 3-letter and/or 1-letter codes used in the art to refer to one of the 20 commonly used L-amino acids.

Notwithstanding that the numerical ranges and approximations of parameters set forth the broad scope of the application, the numerical values setting forth in the specific examples are described as precisely as possible. Any numerical value, however, inherently contains certain errors inevitably resulting from the standard deviation found in their respective measurements. Additionally, all ranges disclosed herein are to be understood to encompass any and all subranges subsumed therein. For example, a stated range of "1 to 10" should be considered to include any or all subranges between a minimum value of 1 and a maximum value of 10 (containing endpoint); that is, all subranges beginning with a minimum value of 1 or greater, such as 1 to 6.1, and subranges that end at a maximum value of 10 or less, such as 5.5 to 10. Additionally, any reference referred to as "incorporated herein" should be understood to be incorporated in its entirety.

In a broad sense, "an antibody" may refer to an immunoglobulin molecule capable of specifically binding to a target via at least one antigen recognition site located in the variable region of the immunoglobulin molecule, thus encompassing a whole antibody, an antibody single chain, or any antigen-binding fragment of an antibody (also referring to "an antigen-binding part"). When the "antibody" and "antigen-binding fragment/antigen-binding part" appear in the same context, the "antibody" can be understood as a complete body relative to the "antigen-binding fragment/antigen-binding part", and both together correspond to the generalized antibody concept.

"A full-length antibody" refers to a protein comprising at least two heavy (H) chains and two light (L) chains interconnected by disulfide bonds. Each heavy chain comprises a heavy chain variable region (abbreviated as VH) and a heavy chain constant region. The heavy chain constant region comprises three domains, CH1, CH2 and CH3. Each light chain comprises a light chain variable region (abbreviated as VL) and a light chain constant region. The light chain constant region comprises one domain, CL. The VH and VL regions can be subdivided into a variety of regions having high variability which are called complementarity determining regions (CDRs), and variety of conserved a more regions interspersed between complementarity-determining regions which are called framework regions (FRs). Each of VH and VL consists of three CDRs and four FRs, arranged from amino-terminal to carboxyl-terminal in the following order: FR1, CDR1, FR2, CDR2, FR3, CDR3, and FR4. These variable regions of the heavy and light chains contain the binding domains that interact with the antigen. The constant region of the antibody can mediate the binding of the immunoglobulin to a host tissue or factor, including various cells of the immune system (such as effector cells) and the first component of the classical complement system (Clq). The full-length antibody may be of any class of antibody, such as IgD, IgE, IgG, IgA, or IgM (or subclasses of the above), but the antibody need not belong to any particular class. Depending on the antibody amino acid sequence of the constant domain of the heavy chain, immunoglobulins can be assigned to different classes. In general, there are five main classes of immunoglobulins: IgA, IgD, IgE, IgG, and IgM, and several of these classes can be further divided into subclasses (isotypes), such as IgG1, IgG2, IgG3, IgG4, IgA1 and IgA2. The heavy chain constant domains that correspond to the different classes of immunoglobulins are called α, δ, ε, γ, and μ, respectively. The subunit structures and three-dimensional structures of the different classes of immunoglobulins are well known. Chimeric or humanized antibodies are also encompassed by antibodies according to the present application. It is well known to those skilled in the art that complementarity determining regions (CDRs, usually CDR1, CDR2 and CDR3) are regions in the variable region that have the greatest influence on the affinity and specificity of antibodies. There are two common ways to define the amino acid sequences of the CDRs of VH or VL, namely Chothia definition and kabat definition. For the amino acid sequence of the variable region of a given antibody, the amino acid sequences of the CDRs in the amino acid sequences of the VH and VL can generally be determined according to the Chothia definition or the Kabat definition. In an embodiment of the present application, Kabat is used to define the amino acid sequences of the CDRs. For the amino acid sequence of the variable region of a given antibody, the amino acid sequences of the CDRs in the amino acid sequence of the variable region can be analyzed in various ways, for example, they can be determined using the online software Abysis (www.abysis.org).

The term "antigen-binding fragment" as used herein refers in particular to an antibody fragment such as Fv, Fab, $F(ab')_2$ or Fab', or any fragment whose half-life can be increased by chemical modification or by incorporation into an liposome. Preferably, said functional fragment will consist of or comprise the partial sequences of the variable chain of the heavy or light chain of the antibody from which it is derived, and the partial sequences are sufficient to retain the same binding specificity and sufficient affinity as the antibody from which they are derived. Such a functional fragment will comprise a minimum of 5 amino acids, preferably 10, 15, 25, 50 and 100 contiguous amino acids of the antibody sequence from which it is derived. Examples of antigen-binding fragments include, but are not limited to: (1) a Fab fragment, which may be a monovalent fragment having a VL-CL chain and a VH-CH1 chain; (2) a $F(ab')_2$ fragment, which may be a bivalent fragment having two Fab' fragments, wherein the two Fab' fragments are connected by a disulfide bridge at the hinge region (i.e. a dimer of Fab'); (3) a Fv fragment with the VL and VH domains of a single arm of an antibody.

The term "single-chain antibody (scFv)" refers to a single polypeptide chain that is connected by a VH domain and a VL domain via a peptide linker. $(scFv)_2$ comprises two VH domains connected by a peptide linker and two VL domains, and the two VL domains are combined with the two VH domains via a disulfide bridge.

The term "Fc fragment", "Fc domain", "Fc portion" or the like refers to a portion of the constant region of an antibody heavy chain, including the hinge, and the CH2 and CH3 fragments of the constant region.

The term "specific binding" as used herein refers to a non-random binding reaction between two molecules, e.g. binding of an antibody to an antigenic epitope.

The term "humanized antibody" means an antibody obtained by grafting CDR sequences derived from another mammalian species, such as a mouse, onto human framework sequences. Additional framework region modifications can be made in the human framework sequences. The humanized antibodies or fragments thereof according to the present application can be prepared by techniques known to those skilled in the art.

The term "chimeric antibody" refers to an antibody in which the variable region sequences are from one species and the constant region sequences are from another species, e.g., an antibody in which the variable region sequences are from a mouse antibody and the constant region sequences are from a human antibody. The chimeric antibody or fragment thereof according to the present application can be produced by using gene recombination technology. For example, the chimeric antibodies can be produced by cloning recombinant DNA comprising a promoter and sequences encoding the variable regions of non-human, especially murine monoclonal antibodies according to the present application, and sequences encoding the constant regions of human antibodies. The chimeric antibody of the present application encoded by such a recombinant gene will be, for example, a mouse-human chimera whose specificity is determined by the variable region derived from mouse DNA and whose isotype is determined by the constant region derived from human DNA. For the method of preparing chimeric antibodies, for example, the document of Verhoeyn et al. (BioEssays, 8:74, 1988) can be referred to.

The term "monoclonal antibody" as used herein refers to an antibody obtained from a population of substantially homogeneous antibodies, i.e., the individual antibodies comprising the population are identical except for possible naturally occurring mutations in a small number of individuals. The monoclonal antibodies described herein specifically include "chimeric" antibodies in which a portion of the heavy and/or light chain is identical or homologous to the corresponding amino acid sequence in an antibody derived from a particular species or belonging to a particular class or subclass of antibodies, and the remainder of the heavy and/or light chain is identical or homologous to the corresponding amino acid sequence in an antibody derived from another species or belonging to another antibody class or subclass, and also includes fragments of such antibodies, so long as they express expected biological activity.

The term "bispecific antibody" refers to an antibody that has the ability to bind two epitopes at the same time. The two epitopes can be on different antigens or on the same antigen. Bispecific antibodies can have a variety of structural configurations. For example, a bispecific antibody can be composed of two Fc fragments and two binding parts fused to them respectively (similar to natural antibodies, the difference is that the two arms bind different antigenic targets or epitopes), and the antigen-binding part can be in a form of a single chain antibody (scfv) or in a form of Fab fragment.

The term "pharmaceutical composition" used herein refers to a combination of at least one drug and optionally a pharmaceutically acceptable carrier or adjuvant combined together to achieve a specific purpose. In some embodiments, the pharmaceutical composition includes combinations that are separated in time and/or space, as long as they can work together to achieve the purpose of the present application. For example, the components contained in the pharmaceutical composition (e.g., antibodies, nucleic acid molecules, nucleic acid molecule combinations and/or conjugates according to the present application) may be administered to the individual as a whole, or separately. When the components contained in the pharmaceutical composition are administered to the individual separately, the components may be administered to the individual simultaneously or sequentially. Preferably, the pharmaceutically acceptable carrier is water, buffered aqueous solution, isotonic saline solution such as PBS (phosphate buffer saline), glucose, mannitol, dextrose, lactose, starch, magnesium stearate, cellulose, magnesium carbonate, 0.3% glycerin, hyaluronic acid, alcohol or polyalkylene glycols such as polypropylene glycol, triglycerides, etc. The type of pharmaceutically acceptable carrier used depends inter alia on whether the composition according to the present application is formulated for oral, nasal, intradermal, subcutaneous, intramuscular or intravenous administration. The composition according to the present application may comprise a wetting agent, an emulsifier or a buffer substance as an additive. The pharmaceutical composition or pharmaceutical formulation according to the present application may be administered by any suitable route, for example may be administered orally, nasally, intradermally, subcutaneously, intramuscularly or intravenously.

The term "therapeutically effective amount" or "effective amount" used herein refers to a dose sufficient to demonstrate benefit to a subject to which it is administered. The actual amount administered, as well as the rate and time course of administration, will depend upon the individual condition and severity of the individual being treated. The prescribing of treatment (e.g. decisions on dosage, etc.) is completely the responsibility of and relies on the general practitioner and other medical practitioners to make decisions, usually taking into consideration of the disease being treated, the individual condition of a patient, the site of delivery, the method of administration and other known factors that are known to a physician.

As used herein, the term "individual" refers to a mammal, such as a human, but can also be another animal, such as a wild animal (such as a heron, a stork, a crane, etc.), a domestic animal (such as a duck, a goose, etc.) or an experimental animal (such as an orangutan, a monkey, a rat, a mouse, a rabbit, a guinea pig, a woodchuck, a ground squirrel, etc.).

The term "homology/identity/consistency" with respect to amino acid or nucleic acid sequence is defined as the percentage of residues that are identical in amino acid or nucleotide sequence variants after an alignment of the sequence and an introduction of gap, if desired, to maximum percent homology. Methods and computer programs for alignment are well known in the art.

In general, for the preparation of monoclonal antibodies or functional fragments thereof, especially of murine origin, reference may be made to the techniques described inter alia in the handbook "Antibodies" (Harlow and Lane, Antibodies: A Laboratory Manual, Cold Spring Harbor Laboratory, Cold Spring Harbor NY, pp. 726, 1988) or the technique for preparation from hybridoma cells described by Kohler and Milstein (Nature, 256:495-497, 1975).

In the first aspect, the present application provides an anti-Siglec15 antibody or antigen-binding fragment thereof comprising a heavy chain variable region and a light chain variable region, wherein the heavy chain variable region comprises a heavy chain CDR1 (HCDR1), a heavy chain CDR2 (HCDR2) and heavy chain CDR3 (HCDR3), and the light chain variable region comprises light chain CDR1 (LCDR1), light chain CDR2 (LCDR2) and light chain CDR3 (LCDR3), wherein:

- the heavy chain variable region comprises HCDR1 having the amino acid sequence set forth in SEQ ID NO: 6, HCDR2 having the amino acid sequence set forth in SEQ ID NO: 7 and HCDR3 having the amino acid sequence set forth in SEQ ID NO: 8, and the light chain variable region comprises LCDR1 having the amino acid sequence set forth in SEQ ID NO: 9, LCDR2 having the amino acid sequence set forth in SEQ ID NO: 10 and LCDR3 having the amino acid sequence set forth in SEQ ID NO: 11; or
- the heavy chain variable region comprises HCDR1 having the amino acid sequence set forth in SEQ ID NO: 6, HCDR2 having the amino acid sequence set forth in SEQ ID NO: 12 and HCDR3 having the amino acid sequence set forth in SEQ ID NO: 8, and the light chain variable region comprises LCDR1 having the amino acid sequence set forth in SEQ ID NO: 13, LCDR2 having the amino acid sequence set forth in SEQ ID NO: 10 and LCDR3 having the amino acid sequence set forth in SEQ ID NO: 11; or
- the heavy chain variable region comprises HCDR1 having the amino acid sequence set forth in SEQ ID NO: 14, and HCDR2 having the amino acid sequence set forth in SEQ ID NO: 15 and HCDR3 having the amino acid sequence set forth in SEQ ID NO: 16, and the light chain variable region comprises LCDR1 having the amino acid sequence set forth in SEQ ID NO: 17, LCDR2 having the amino acid sequence set forth in SEQ ID NO: 18 and LCDR3 having the amino acid sequence set forth in SEQ ID NO: 19; or
- the heavy chain variable region comprises HCDR1 having the amino acid sequence set forth in SEQ ID NO: 20, HCDR2 having the amino acid sequence set forth in SEQ ID NO: 21 and HCDR3 having the amino acid sequence set forth in SEQ ID NO: 22, and the light chain variable region comprises LCDR1 having the amino acid sequence set forth in SEQ ID NO: 23, LCDR2 having the amino acid sequence set forth in SEQ ID NO: 24 and LCDR3 having the amino acid sequence set forth in SEQ ID NO: 25,
- wherein the amino acid sequences of HCDR1, HCDR2, HCDR3 and LCDR1, LCDR2, LCDR3 are defined according to Kabat.

In some embodiments of the first aspect, the heavy chain variable region has the amino acid sequence set forth in SEQ ID NO: 26, 28, 30 or 32 or the amino acid sequence having at least 80%, 81%, 82%, 83%, 84%, 85%, 86%, 87%, 88%, 89%, 90%, 91%, 92%, 93%, 94%, 95%, 96%, 97%, 98% or 99% homology with the amino acid sequence set forth in SEQ ID NO: 26, 28, 30 or 32.

In some embodiments of the first aspect, the light chain variable region has the amino acid sequence set forth in SEQ ID NO: 27, 29, 31 or 33 or the amino acid sequence having at least 80%, 81%, 82%, 83%, 84%, 85%, 86%, 87%, 88%, 89%, 90%, 91%, 92%, 93%, 94%, 95%, 96%, 97%, 98% or 99% homology with the amino acid sequence set forth in SEQ ID NO: 27, 29, 31 or 33.

In some embodiments of the first aspect, the heavy chain variable region has the amino acid sequence set forth in SEQ ID NO:26, and the light chain variable region has the amino acid sequence set forth in SEQ ID NO:27.

In some embodiments of the first aspect, the heavy chain variable region has the amino acid sequence set forth in SEQ ID NO:28, and the light chain variable region has the amino acid sequence set forth in SEQ ID NO:29.

In some embodiments of the first aspect, the heavy chain variable region has the amino acid sequence set forth in SEQ ID NO:30, and the light chain variable region has the amino acid sequence set forth in SEQ ID NO:31.

In some embodiments of the first aspect, the heavy chain variable region has the amino acid sequence set forth in SEQ ID NO:32 and the light chain variable region has the amino acid sequence set forth in SEQ ID NO:33.

In a second aspect, the present application provides an anti-Siglec15 antibody or antigen-binding fragment thereof that specifically binds to a polypeptide having the amino acid sequence described in any one of (a) to (e):

(a) the amino acid sequence set forth in SEQ ID NO: 1;
(b) the amino acid sequence consisting of amino acid residues at positions 20 to 328 in the amino acid sequence set forth in SEQ ID NO: 1;
(c) the amino acid sequence consisting of amino acid residues at positions 1 to 263 in the amino acid sequence set forth in SEQ ID NO: 1;
(d) the amino acid sequence consisting of amino acid residues at positions 20 to 263 in the amino acid sequence set forth in SEQ ID NO: 1;
(e) the amino acid sequence having substitution, deletion or addition of one or more amino acid residues in the amino acid sequences described in (a) to (d).

The full-length amino acid sequence of human Siglec15 is set forth in SEQ ID NO: 1, wherein positions 1-19 are a signal peptide sequence, positions 20-263 are an extracellular domain (ECD), positions 40-158 are IgV domain, positions 168-251 are IgC2 domain. Therefore, the amino acid sequences described in (a) to (d) above include the full-length amino acid sequence of human Siglec15, and various human Siglec15 fragments, all of which include the extracellular domain, that is, the binding domain of the antibody of the present application.

In a third aspect, the present application provides an anti-Siglec15 antibody or antigen-binding fragment thereof comprising a heavy chain variable region and a light chain variable region, wherein the heavy chain variable region has the amino acid sequence having at least 80%, 81%, 82%, 83%, 84%, 85%, 86%, 87%, 88%, 89%, 90%, 91%, 92%, 93%, 94%, 95%, 96%, 97%, 98% or 99% homology with the amino acid sequence set forth in SEQ ID NO: 26, 28, 30 or 32, and the light chain variable region has the amino acid sequence set forth in SEQ ID NO: 27, 29, 31 or 33 or the amino acid sequence having at least 80%, 81%, 82%, 83%, 84%, 85%, 86%, 87%, 88%, 89%, 90%, 91%, 92%, 93%, 94%, 95%, 96%, 97%, 98% or 99% homology with the amino acid sequence set forth in SEQ ID NO: 27, 29, 31 or 33.

In some embodiments of the third aspect, he heavy chain variable region has the amino acid sequence having at least 80%, 81%, 82%, 83%, 84%, 85%, 86%, 87%, 88%, 89%, 90%, 91%, 92%, 93%, 94%, 95%, 96%, 97%, 98% or 99% homology with the amino acid sequence set forth in SEQ ID NO: 26, and the light chain variable region has the amino acid sequence having at least 80%, 81%, 82%, 83%, 84%, 85%, 86%, 87%, 88%, 89%, 90%, 91%, 92%, 93%, 94%, 95%, 96%, 97%, 98% or 99% homology with the amino acid sequence set forth in SEQ ID NO: 27.

In some embodiments of the third aspect, he heavy chain variable region has the amino acid sequence having at least 80%, 81%, 82%, 83%, 84%, 85%, 86%, 87%, 88%, 89%, 90%, 91%, 92%, 93%, 94%, 95%, 96%, 97%, 98% or 99% homology with the amino acid sequence set forth in SEQ ID NO: 28, and the light chain variable region has the amino acid sequence having at least 80%, 81%, 82%, 83%, 84%, 85%, 86%, 87%, 88%, 89%, 90%, 91%, 92%, 93%, 94%, 95%, 96%, 97%, 98% or 99% homology with the amino acid sequence set forth in SEQ ID NO: 29.

In some embodiments of the third aspect, he heavy chain variable region has the amino acid sequence having at least 80%, 81%, 82%, 83%, 84%, 85%, 86%, 87%, 88%, 89%, 90%, 91%, 92%, 93%, 94%, 95%, 96%, 97%, 98% or 99% homology with the amino acid sequence set forth in SEQ ID NO: 30, and the light chain variable region has the amino acid sequence having at least 80%, 81%, 82%, 83%, 84%, 85%, 86%, 87%, 88%, 89%, 90%, 91%, 92%, 93%, 94%, 95%, 96%, 97%, 98% or 99% homology with the amino acid sequence set forth in SEQ ID NO: 31.

In some embodiments of the third aspect, he heavy chain variable region has the amino acid sequence having at least 80%, 81%, 82%, 83%, 84%, 85%, 86%, 87%, 88%, 89%, 90%, 91%, 92%, 93%, 94%, 95%, 96%, 97%, 98% or 99% homology with the amino acid sequence set forth in SEQ ID NO: 32, and the light chain variable region has the amino acid sequence having at least 80%, 81%, 82%, 83%, 84%, 85%, 86%, 87%, 88%, 89%, 90%, 91%, 92%, 93%, 94%, 95%, 96%, 97%, 98% or 99% homology with the amino acid sequence set forth in SEQ ID NO: 33.

In a fourth aspect, the present application provides an anti-Siglec15 antibody or antigen-binding fragment thereof that comprises a heavy chain variable region and a light chain variable region, wherein the heavy chain variable region comprises a heavy chain CDR1 (HCDR1), a heavy chain CDR2 (HCDR2) and heavy chain CDR3 (HCDR3), wherein the heavy chain variable region comprises HCDR1 having the amino acid sequence set forth in SEQ ID NO: 6, HCDR2 having the amino acid sequence set forth in SEQ ID NO: 7 and HCDR3 having the amino acid sequence set forth in SEQ ID NO: 8; or the heavy chain variable region comprises HCDR1 having the amino acid sequence set forth in SEQ ID NO: 6, HCDR2 having the amino acid sequence set forth in SEQ ID NO: 12 and HCDR3 having the amino acid sequence set forth in SEQ ID NO: 8; or the heavy chain variable region comprises HCDR1 having the amino acid sequence set forth in SEQ ID NO: 14, HCDR2 having the amino acid sequence set forth in SEQ ID NO: 15, and HCDR3 having the amino acid sequence set forth in SEQ ID NO: 16; or the heavy chain variable region comprises HCDR1 having the amino acid sequence set forth in SEQ ID NO: 20 HCDR2 having the amino acid sequence set forth in SEQ ID NO: 21 and HCDR3 having the amino acid sequence set forth in SEQ ID NO: 22, wherein the amino acid sequences of HCDR1, HCDR2, and HCDR3 are defined according to Kabat.

An example of the antibody of the fourth aspect is a single-domain antibody, also known as a variable domain of heavy chain of heavy-chain antibody (VHH), which consists of only one heavy chain variable region, also known as a nanobody. VHH antibody is a natural light chain-deficient antibody originally found in the peripheral blood of an alpaca, and it contains only one heavy chain variable region (VHH) and two conventional CH2 and CH3 regions. The cloned and expressed VHH structure has the same structural stability and antigen-binding activity as the original heavy chain antibody, and is the smallest known unit that can bind the target antigen.

In some embodiments of the first to fourth aspects, the amino acid sequence of the heavy chain variable region differs from the amino acid sequence set forth in SEQ ID NO: 26, 28, 30 or 32 by about 1, 2, 3, 4, 5, 6, 7, 8, 9 or 10 amino acid substitution, deletion and/or addition. In some embodiments, about 1, 2, 3, 4, 5, 6, 7, 8, 9, 10, 11, 12, 13, 14, 15, 20, 25 or more amino acids may be truncated from the C-terminal or N-terminal region of the amino acid sequence set forth in SEQ ID NO: 26, 28, 30 or 32, while a similar function of the heavy chain variable region of the antibody is still maintained. In some embodiments, 1, 2, 3, 4, 5, 6, 7, 8, 9, 10, 11, 12, 13, 14, 15, 20, 25 or more amino acids may be added to the C-terminal or N-terminal region of the amino acid sequence set forth in SEQ ID NO: 26, 28, 30 or 32, and the resulting amino acid sequence still maintains a similar function to the heavy chain variable region of the antibody. In some embodiments, 1, 2, 3, 4, 5, 6, 7, 1, 2, 3, 4, 5, 6, 7, 8, 9, 10, 11, 12, 13, 14, 15, 20, 25 or more amino acids may added to or deleted from the regions except C-terminal or N-terminal region of the amino acid sequence set forth in SEQ ID NO: 26, 28, 30 or 32 as long as the altered amino acid sequence substantially maintains a similar function of the heavy chain variable region of the antibody.

In some embodiments of the first to fourth aspects, the amino acid sequence of the light chain variable region differs from the amino acid sequence set forth in SEQ ID NO: 27, 29, 31 or 33 by about 1, 2, 3, 4, 5, 6, 7, 8, 9 or 10 amino acid substitution, deletion and/or addition. In some embodiments, about 1, 2, 3, 4, 5, 6, 7, 8, 9, 10, 11, 12, 13, 14, 15, 20, 25 or more amino acids may be truncated from the C-terminal or N-terminal region of the amino acid sequence set forth in SEQ ID NO: 27, 29, 31 or 33, while a similar function of the light chain variable region of the antibody is still maintained. In some embodiments, 1, 2, 3, 4, 5, 6, 7, 8, 9, 10, 11, 12, 13, 14, 15, 20, 25 or more amino acids may be added to the C-terminal or N-terminal region of the amino acid sequence set forth in SEQ ID NO: 27, 29, 31 or 33, and the resulting amino acid sequence still maintains a similar function to the light chain variable region of the antibody. In some embodiments, 1, 2, 3, 4, 5, 6, 7, 1, 2, 3, 4, 5, 6, 7, 8, 9, 10, 11, 12, 13, 14, 15, 20, 25 or more amino acids may added to or deleted from the regions except C-terminal or N-terminal region of the amino acid sequence set forth in SEQ ID NO: 27, 29, 31 or 33 as long as the altered amino acid sequence substantially maintains a similar function of the light chain variable region of the antibody.

In some embodiments of the first to fourth aspects, the anti-Siglec15 antibody is a complete antibody, a single-chain antibody (scFv) or a bispecific antibody. In some embodiments of the first to fourth aspects, the antigen-binding fragment of the anti-Siglec 15 antibody is Fab, Fab', Fv or $F(ab')_2$. In some embodiments of the first to fourth aspects, the anti-Siglec15 antibody is a murine antibody, a chimeric antibody, a humanized antibody or a human antibody. In some embodiments of the first to fourth aspects, the anti-Siglec 15 antibody is a monoclonal antibody. In some embodiments of the first to fourth aspects, the anti-Siglec15 antibody is a bispecific antibody. In some embodiments of the first to fourth aspects, the anti-Siglec15 antibody is of IgG1, IgG2 or IgG4 isotype, i.e., the antibody comprises a heavy chain constant region of IgG1 subtype, IgG2 subtype or IgG4 subtype. In some specific embodiments, the anti-Siglec 15 antibody is of the IgG1 isotype. In some embodiments of the first to fourth aspects, the anti-Siglec15 antibody comprises a light chain constant region of a kappa or lambda subtype.

In a fifth aspect, the present application provides an immunoconjugate (also known as Antibody-Drug Conjugate (ADC)) comprising the anti-Siglec15 antibody or antigen-binding fragment thereof described in the first to fourth aspects conjugated to a therapeutic agent.

In some embodiments of the fifth aspect, the therapeutic agent is an antitumor drug, e.g., a cytotoxic drug, an immunopotentiator, or a radioisotope.

In some embodiments, the type of cytotoxic drug includes a tubulin inhibitor (e.g., an alkaloid), a DNA topoisomerase inhibitor, a DNA damaging agent, an antimetabolite, or an antitumor antibiotic.

In some embodiments, the tubulin inhibitors includes, but is not limited to, an auristatin derivative (e.g., MMAE (Monomethyl auristatin E), MMAF (Monomethyl auristatin F)) or a maytansine alkaloid derivative (e.g., DM1, DM4, Ansamitocin, Mertansine or dolastatin and a derivative thereof).

In some embodiments, the DNA topoisomerase inhibitor is a camptothecin analog or a DNA topoisomerase I inhibitor and a derivative thereof, e.g., DXD, SN38, irinotecan, irinotecan hydrochloride, camptothecin, 9-aminocamptothecin, 9-nitrocamptothecin, 10-hydroxycamptothecin, 9-chloro-10-hydroxycamptothecin, 22-hydroxyacuminatine, topotecan, lurtotecan, belotecan, exatecan, homosilatecan, 6,8-dibromo-2-methyl-3-[2-(D-xylopyranosylamino)phenyl]-4(3H)-quinazolinone, 2-cyano-3-(3,4-dihydroxyphenyl)-N-(phenylmethyl)-(2E)-2-acrylamide, 2-cyano-3-(3,4-dihydroxyphenyl)-N-(3-hydroxyphenylpropyl)-(E)-2-acrylamide, 12-β-D-glucopyranosyl-12,13-dihydro-2,10-dihydroxy-6-[[2-hydroxy-1-(hydroxymethyl)ethyl]amino]-5H-indolo[2,3-a]pyrrolo[3,4-c]carbazole-5,7(6H)-dione, N-[2-(dimethylamino)ethyl]-4-acridinecarboxamide dihydrochloride, N-[2-(dimethylamino)ethyl]-4-acridinecarboxamide.

In some embodiments, the DNA damaging agent includes, but is not limited to, calicheamicins, duocarmycins, antramycin derivatives PBD (pyrrolobenzodiazepine).

In some embodiments, the antimetabolite includes, but is not limited to, methotrexate, 6-mercaptopurine, or 5-fluorouracil.

In some embodiments, the antitumor antibiotic includes, but is not limited to, polypeptide antibiotics (e.g., actinomycin D or bleomycin) or anthraquinones (e.g., doxorubicin or mitoxantrone hydrochloride). In some embodiments, the radioactive isotope includes, but is not limited to, 211At, 131I, 125I, 90Y, 186Re, 188Re, 153Sm, 212Bi, 32P, 60Co, or 177Lu.

In some embodiments, the immune potentiating agent includes, but is not limited to, levamisole, pidotimod, imiquimod, isoprinosine, Poly I:C, or Poly U.

In some embodiments, the anti-Siglec15 antibody of the present application is covalently linked to the drug moiety via a linker. In some embodiments, the linker is a cleavable linker. In some embodiments, the linker is cleavable under intracellular conditions. In one embodiment, the linker is hydrolyzable at a pH of less than 5.5. In some embodiments, the linker is cleavable by an intracellular protease. In some embodiments, the linker is a cleavable linker by a cathepsin. In some embodiments, the linker comprises a dipeptide. In some embodiments, the dipeptide is valine (Val)-citrulline (Cit). In some embodiments, the antibody is attached to the linker through the thiol group of a cysteine of the antibody. In some embodiments, the antibody is attached to the linker through an amino group (particularly of glutamine residue) of the antibody. Non-limiting examples of the linker include mc-Val-Cit-pAB, mc-Val-Cit-pABC, mc-Val-Cit, $NH_2$-(PEG)m-Val-Cit, $NH_2$-(PEG)m-Val-Cit-pAB, wherein m is an integer from 1 to 8.

In a sixth aspect, the present application provides a pharmaceutical composition comprising the anti-Siglec15 antibody or antigen-binding fragment thereof described in the first to fourth aspects or the immunoconjugate described in the fifth aspect, and a pharmaceutically acceptable excipient, diluent agent or carrier.

In some embodiments, the pharmaceutical composition may also contain one or more from a group consisting of: a lubricant such as talc, magnesium stearate, and mineral oil; a wetting agent; an emulsifying agent; a suspending agent; a preservative such as benzoic acid, sorbic acid and calcium propionate; a sweetener and/or a flavoring agent, etc. In some embodiments, the pharmaceutical composition of the present application can be formulated as a tablet, a pill, a powder, a lozenge, an elixir, a suspension, an emulsion, a solution, a syrup, a suppository or a capsule and the like.

In some embodiments, the pharmaceutical composition of the present application can be delivered by any physiologically acceptable mode of administration, including but not limited to: an oral administration, a parenteral administration, a nasal administration, a rectal administration, an intraperitoneal administration, an intravascular injection, a subcutaneous administration, a transdermal administration, an inhalation administration, etc.

In some embodiments, the pharmaceutical composition for therapeutic use may be formulated in the form of a lyophilized formulation or an aqueous solution by mixing a reagent of desired purity with, as appropriate, a pharmaceutically acceptable carrier, excipient, etc. and is used for storage.

In some embodiments of the sixth aspect, the pharmaceutical composition is used to regulate the immune response in an individual, reverse the inhibition of Siglec15 protein on the proliferation of PBMC lymphocytes, reverse the inhibition of Siglec15 protein on the secretion of IFN-γ from PBMC lymphocytes, and inhibit growth of tumor cells in an individual or treat a hyperproliferative disease (for example, a hyperproliferative disease associated with aberrant expression of Siglec15). In some embodiments, the hyperproliferative disease is a tumor, e.g., a tumor associated with aberrant expression of Siglec15.

In some embodiments of the sixth aspect, the pharmaceutical composition of the sixth aspect is used to treat a tumor in combination with an anti-PD-1 or anti-PD-L1 antibody.

In a seventh aspect, the present application provides a use of the anti-Siglec 15 antibody or antigen-binding fragment thereof described in the first to fourth aspects or the immunoconjugate described in the fifth aspect in the preparing a medicament for regulating the immune response in an individual, reversing the inhibition of Siglec15 protein on the proliferation of PBMC lymphocytes, reversing the inhibition of Siglec15 protein on the secretion of IFN-γ from PBMC lymphocytes, and inhibiting growth of tumor cells in an individual or treating a hyperproliferative disease (for example, a hyperproliferative disease associated with aberrant expression of Siglec15). In some embodiments, the hyperproliferative disease is a tumor, e.g., a tumor associated with aberrant expression of Siglec15.

In some embodiments of the seventh aspect, the medicament further comprises an anti-PD-1 or anti-PD-L1 antibody.

In an eighth aspect, the present application provides a method for regulating the immune response in an individual, reversing the inhibition of Siglec15 protein on the proliferation of PBMC lymphocytes, reversing the inhibition of Siglec15 protein on the secretion of IFN-γ from PBMC lymphocytes, and inhibiting growth of tumor cells in an individual or treating a hyperproliferative disease (for example, a hyperproliferative disease associated with aberrant expression of Siglec15), comprising administering to an individual in need thereof a therapeutically effective amount of the anti-Siglec15 antibody or antigen-binding fragment thereof described in the first to fourth aspects or the immunoconjugate described in the fifth aspect or the pharmaceutical composition described in the sixth aspect. In some embodiments, the hyperproliferative disease is a tumor, e.g., a tumor associated with aberrant expression of Siglec15.

In some embodiments of the eighth aspect, the method further comprises administering the anti-PD-1 or anti-PD-L1 antibody to the individual in need thereof.

In embodiments of the sixth to eighth aspects, the anti-Siglec15 antibody of the present application can be used to induce, increase or enhance T cell proliferation, and induce T cell response by reducing or preventing Siglec-15 from binding to a counter-receptor on T cells. Up-regulation of the immune system is particularly desirable in the treatment of a cancer and a chronic infection, so the anti-Siglec15 antibodies of the present application can be used to treat such conditions. The anti-Siglec15 antibody, immunoconjugate or pharmaceutical composition of the present application can be used to treat or prevent various cancers or other abnormal proliferative diseases, including (but not limited to): cancer, including a bladder cancer, a breast cancer, a colon cancer, a kidney cancer, a liver cancer, a lung cancer, an ovary cancer, a pancreas cancer, a stomach cancer, a cervix cancer, a thyroid cancer, and a skin cancer; including a squamous cell carcinoma; a lymphoid lineage hematopoietic system tumo, including aleukemia, an acute lymphoblastic leukemia, an acute lymphoblastic leukemia, a B-cell lymphoma, a T-cell lymphoma, a Burkitt's lymphoma; a myeloid hematopoietic system tumor, including an acute and chronic myelogenous leukemia and a promyelocytic leukemia; a mesenchymal origin tumor, including a fibrosarcoma and a rhabdomyosarcoma; a central and peripheral nervous system tumor, including an astrocytoma, a neuroblastoma, a glioma, and a schwannoma; a mesenchymal origin tumor, including fibrosarcoma, rhabdomyosarcoma and osteosarcoma; and other tumors, including a melanoma, a xeroderma pigmentosum, a keratoacanthoma, a seminoma, a follicular carcinoma of thyroid, and a teratocarcinoma.

The anti-Siglec15 antibody, immunoconjugate or pharmaceutical composition of the present application can be used to treat infections and infectious diseases. Generally, the method comprises stimulating or enhancing an immune response to an infection-initiating agent, reducing or preventing the progression of an infectious disease, or a combination thereof, by administering to the subject an amount of a Siglec-15 binding molecule. The method may reduce one or more symptoms of infection. Infections or diseases can be caused by bacterums, viruses, protozoans, worms or other microbial pathogens that enters a cell and is attacked by a cytotoxic T lymphocyte. The infection or disease can be acute or chronic. The acute infection is usually an infection of short duration. During acute microbial infection, the immune cells begin to express immunomodulatory receptors. Accordingly, in some embodiments, the method comprises enhancing an immune stimulatory response to an acute infection.

In a ninth aspect, the present application provides an isolated polynucleotide encoding the anti-Siglec15 antibody or antigen-binding fragment described in the first to fourth aspects. In some embodiments, the polynucleotide is operably linked to a regulatory sequence that is recognized by a host cell transformed with the vector.

In a tenth aspect, the present application provides a vector (e.g., an expression vector) comprising a polynucleotide encoding the anti-Siglec15 antibody or antigen-binding fragment described in the first to fourth aspects. The selection of expression vector depends on the selection of the host cell and can be selected so as to have the desired expression and regulatory characteristics in the host cell selected.

The term "expression vector" is a vector that includes one or more expression control sequences, which are DNA sequences that control and regulate the transcription and/or translation of another DNA sequence.

The nucleic acid in the vector may be operably linked to one or more expression control sequences. As used herein, "operably linked" means incorporated into a genetic construct such that expression control sequences effectively control the expression of a coding sequence of interest. Examples of expression control sequences include promoters, enhancers, and transcription termination regions. The promoter is an expression control sequence consisting of a region of a DNA molecule usually within 100 nucleotides upstream of the start of transcription (usually near the initiation site for RNA polymerase II). In order for a coding sequence to be under the control of a promoter, the translation initiation site of the translational reading frame of the polypeptide must be positioned between 1 and about 50 nucleotides downstream of the promoter. The Enhancer provides expression specificity in terms of time, location and level. Unlike the promoter, the enhancer can function when located at different distances from the transcription site. The enhancer can also be located downstream of the transcription initiation site. A coding sequence is "operably linked to" and "under the control of" an expression control sequence in a cell when RNA polymerase is capable of transcribing the coding sequence into mRNA, which can then be translated into the protein encoded by the coding sequence.

Suitable expression vector includes, but is not limited to, plasmid and viral vectors derived from, for example, a bacteriophage, a baculovirus, a tobacco mosaic virus, a herpes virus, a cytomegalovirus, a retrovirus, a vaccinia virus, an adenovirus, and an adeno-associated virus. Many vectors and expression systems are commercially available from companies such as Novagen (Madison, WI), Clontech (Palo Alto, CA), Stratagene (LaJolla, CA), and Invitrogen Life Technologies (Carlsbad, CA), etc.

The Expression vector can include a tag sequence. The tag sequence is usually expressed as fusions to the encoded polypeptide. Such a tag can be inserted anywhere within the polypeptide, including the carboxyl or amino terminal. Examples of useful tags include, but are not limited to, a Fc fragment, a polyhistidine, a green fluorescent protein (GFP), a glutathione S-transferase (GST), a c-myc, a hemagglutinin, a Flag™ tag (Kodak, New Haven, CT), a maltose E-binding protein and a protein A. In some embodiments, a nucleic acid molecule encoding a Siglec-15 fusion polypeptide is present in a vector containing nucleic acid encoding one or more domains of an Ig heavy chain constant region, e.g., corresponding to the amino acid sequences (Fc fragment) of the hinge region, CH2 region and CH3 region of human immunoglobulin Cγ1 chain.

In an eleventh aspect, the present application provides an isolated host cell comprising the vector described in the tenth aspect.

In some embodiments, the host cell can be a prokaryotic host cell, a eukaryotic host cell, or a phage. The prokaryotic host cell can be *Escherichia coli, Bacillus subtilis, Streptomyces* or *Proteus mirabilis*, etc. The eukaryotic host cell can be fungus such as *Pichia pastoris, Saccharomyces cerevisiae, Schizosaccharomyces, Trichoderma*, an insect cell such as armyworm, a plant cell such as a tobacco, a mammalian cell such as BHK cell, CHO cell, COS cell, myeloma cell and the like.

In a twelfth aspect, the present application provides a method for preparing the anti-Siglec15 antibody or antigen-binding fragment thereof described in the first to fourth aspects, comprising a step of culturing the host cell described in the eleventh aspect. In some embodiments of the twelfth aspect, the method further comprises the step of isolating the anti-Siglec15 antibody or antigen-binding fragment thereof.

It should be understood that the above detailed description is only for making those skilled in the art understand the content of the present application more clearly, and is not intended to limit in any respect. Various modifications and changes to the described embodiments can be made by those skilled in the art.

EXAMPLE

The following examples are for the purpose of illustration only and not limiting the scope of the application.

Example 1, Preparation of Siglec15 Antigen and Detection Protein

The inventors of the present application used Uniprot (Q6ZMC9) to obtain the amino acid sequences of Siglec 15 antigen for immunization and Siglec 15 protein for detection. The Ig V region or the full-length extracellular region of Siglec15 was recombined with the human IgG1 Fc fragment of IgG antibody heavy chain or 7 histidines (His), respectively, and cloned into the pCDNA3.1 vector (Nanjing GenScript Biotechnology Co., Ltd.). The above plasmid was transfected into Hek293F mammalian cells by PEI transfection method, and on day7 after transfection, the cell supernatant was collected for purification. They were named Siglec15-IgV-Fc, Siglec15-ECD-Fc or Siglec15-ECD-His respectively, and their amino acid sequences are shown below.

The full-length amino acid sequence of human Siglec15 (SEQ ID NO: 1) is as follows, in which positions 1-19 are the signal peptide sequence, positions 20-263 are the extracellular domain (indicated by italic and bold letters), and positions 40-158 are the IgV domain (indicated by a single underline), and positions 168-251 are IgC2 domain (indicated by a double underline):

MEKSIWLLACLAWVLPTGS*FVRTKIDTTENLLNTEVHSSPAQRWSMQ*

*VPPEVSAEAGDAAVLPCTFTHPHRHYDGPLTAIWRAGEPYAGPQVFR*

*CAAARGSELCQTALSLHGRFRLLGNPRRNDLSLRVERLALADDRRYF*

*CRVEFAGDVHDRYESRHGVRLHVTAAPRIVNISVLPSPAHAFRALCT*

*AEGEPPPALAWSGPALGNSLAAVRSPREGHGHLVTAELPAL*

*THDGRYTCTAANSLGRSEASVYLFRFHGASGAST*VALLLGALGFK

ALLLLGVLAARAARRRPEHLDTPDTPPRSQAQESNYENLSQMNPRSP

PATMCSP

The amino acid sequence (SEQ ID NO: 2) of Siglec15-ECD-Fc is as follows, wherein positions 1-19 are the signal peptide; positions 20-263 are the Siglec 15 extracellular domain (ECD) (indicated by italic and bold letters); positions 264-494 are the Fc tag:

MEKSIWLLACLAWVLPTGS*FVRTKIDTTENLLNTEVHSSPAQRWSMQVPP*

*EVSAEAGDAAVLPCTFTHPHRHYDGPLTAIWRAGEPYAGPQVFRCAAARG*

*SELCQTALSLHGRFRLLGNPRRNDLSLRVERLALADDRRYFCRVEFAGDV*

*HDRYESRHGVRLHVTAAPRIVNISVLPSPAHAFRALCTAEGEPPPALAWS*

*GPALGNSLAAVRSPREGHGHLVTAELPALTHDGRYTCTAANSLGRSEASV*

*YLFRFHGASGAST*PKSCDKTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPP

SRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK

The amino acid sequence (SEQ ID NO: 3) of Siglec15-IgV-Fc is as follows, wherein positions 1-19 are the signal peptide; positions 40-158 are the IgV region of Siglec15 (indicated by italic and bold letters); positions 166-396 are Fc tag:

MEKSIWLLACLAWVLPTGSFVRTKIDTTENLLNTEVHSS*PAQRWSMQVPP*

*EVSAEAGDAAVLPCTFTHPHRHYDGPLTAIWRAGEPYAGPQVFRCAAARG*

*SELCQTALSLHGRFRLLGNPRRNDLSLRVERLALADDRRYFCRVEFAGDV*

*HDRYESRH*GVRLHVTPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

The Siglec15-ECD-His (SEQ ID NO: 4) is used as the detection reagent of the present application, and its amino acid sequence is as follows, wherein positions 1-19 are the signal peptide; positions 20-263 are the Siglec15 extracellular domain (ECD) (indicated by italic and bold letters); positions 264-270 are histidine tag:

MEKSIWLLACLAWVLPTGS*FVRTKIDTTENLLNTEVHSSPAQRWSMQVPP*

*EVSAEAGDAAVLPCTFTHPHRHYDGPLTAIWRAGEPYAGPQVFRCAAARG*

*SELCQTALSLHGRFRLLGNPRRNDLSLRVERLALADDRRYFCRVEFAGDV*

*HDRYESRHGVRLHVTAAPRIVNISVLPSPAHAFRALCTAEGEPPPALAWS*

*GPALGNSLAAVRSPREGHGHLVTAELPALTHDGRYTCTAANSLGRSEASV*

*YLFRFHGASGAST*HHHHHHH

Example 2, Purification of Recombinant Protein or Antibody 2.1 Purification of Recombinant Protein with His Tag The cell expression supernatant was centrifuged at high speed to remove the precipitate, and the supernatant was collected. The nickel column was pre-equilibrated with HBS buffer (10 mM HEPES pH 7.5, 500 mM NaCl) containing 10 mM imidazole, and washed in 2-5 times of column volume, and the supernatant sample was loaded on the nickel column. The column was rinsed with HBS buffer containing 10 mM imidazole until the A280 reading dropped to baseline. Then the chromatographic column was washed with HBS buffer solution containing 20 mM imidazole to remove non-specifically bound heteroproteins, and the effluent was collected. The target protein was then eluted with HBS buffer containing 300 mM imidazole, and the elution peak was collected, and the collected eluate was exchanged into HBS buffer. The Siglec15-ECD-His protein purified by nickel column was used for the screening and performance testing of the antibody of this application.

2.2 Purification of Fc Fusion Protein or Antibody

The cell expression supernatant was centrifuged at high speed to remove the precipitate, and the supernatant was collected. The Protein A/G column was pre-equilibrated with PB buffer and washed in 2-5 times of column volume, and the supernatant sample was loaded on the column. The column rinsed with PB buffer until the A280 reading dropped to baseline. The target protein was eluted by 0.1 M glycine solution at pH 2.7 into neutralization buffer added in advance with 1 M Tris-HCL at pH 9.0, and the collected eluate was exchanged into PBS buffer. The Siglec15-ECD-Fc and Siglec 15-IgV-Fc with Fc fragments were used as immunogens or performance tests of the antibodies of this application. Fusion of the Fc fragment can improve the expression and secretion of the target protein in mammals, and at the same time, the Fc fragment could specifically bind to protein A, which was beneficial to the purification of the fusion protein; in addition, the Fc fragment could also be recognized and bound by the animal anti-human secondary antibody, and can be used to indicate antibody blocking effect.

Example 3, Preparation of Anti-Human Siglec15 Hybridoma Monoclonal Antibody

The healthy BALB/c female mice aged 6-8 weeks were selected, and Siglec15-ECD-Fc and Siglec15-IgV-Fc proteins were used as immunogens respectively. For the first immunization, the mixed emulsion of Freund's complete adjuvant and immune protein was injected subcutaneously at multiple points in the back and groin of mice, and the ratio of immunogen and adjuvant was 1:1, in 100 μg/mouse. Before the initial immunization experiment, a little blood was taken from the mouse eyeball as a negative control for the detection of serum antibody titer. On day 7-10 after the initial immunization, the mixed emulsion of Freund's incomplete adjuvant and immune protein was used for booster immunization in the same way as the initial immunization. Afterwards, booster immunization was carried out 2-3 times every 7-10 days, and the ratio of immunogen and adjuvant was 1:1, in 50 μg/mouse. The peripheral serum of the mice was collected and tested by enzyme-linked immunoassay (ELISA). The specific method was as follows. As shown in FIG. 1, the serum titers of mice immunized with Siglec15-ECD-Fc and Siglec15-IgV-Fc proteins all reached 360,000 or more, and the mice with high plasma antibody titers were selected for cell fusion. On day 3 before fusion, 50 μg immunogen without adjuvant was injected through tail vein or abdominal cavity for pulse immunization. On the day of fusion, the spleen of the mouse was taken out and cultured with RPMI 1640 basal medium (GIBCO company) to prepare a single cell suspension. The SP2/0 cells and spleen cells were mixed at a ratio of 1:3-1:5, and the fusion was carried out by using electrofusion. They were cultured in HAT selective medium for 5-7 days. The medium was replaced with HT medium, and the culturing was continued in 37° C. $CO_2$ incubator.

The specific method for detecting antibody titer or screening monoclonal antibody by ELISA was as follows:

(1) Coating: Siglec15-ECD-His protein was dissolved in antigen coating buffer (pH 9.6, 0.05M carbonate buffer) to a final concentration of 1 μg/mL; and the coated protein was applied to 96-well polystyrene microtiter plate overnight at 4° C.

(2) Blocking: the plate was washed with PBST buffer for three times, PBS solution containing 2% BSA was added to each well, the plate was incubated at 37° C. for 2 h, and then the plate was washed with PBST buffer for three times.

(3) Incubating with primary antibody: mouse serum (or supernatant secreted by hybridoma cells, or purified antibody) was diluted to a series of concentration gradients with 0.2% BSA, and added to the microtiter plate. The serum obtained from the eyeball of the mouse before the initial immunization was used as a negative control, and the blank control was a PBS solution containing 0.2% BSA, and the plate was incubated at 37° C. for 2 h. The plate was washed with PBST buffer for three times.

(4) Incubating with secondary antibody: horseradish peroxidase-labeled goat anti-human IgG was added, and the plate was incubated at 37° C. for 1 hour, and the plate was washed three times with PBST buffer.

(5) Color development: TMB substrate color development solution A and solution B were mixed, 100 μL of mixed solution was added to each well, and the reaction was carried out at room temperature for 10 minutes in the dark.

(6) Termination: 100 μL of 2M $H_2SO_4$ was added to each well to terminate the color reaction.

(7) Detection: the microplate reader was used to detect the absorbance value of each well of the microplate plate, and the detection wavelength is 450 nm.

Example 4, Screening and Characterization of Hybridoma Cell Lines

Figure 2:
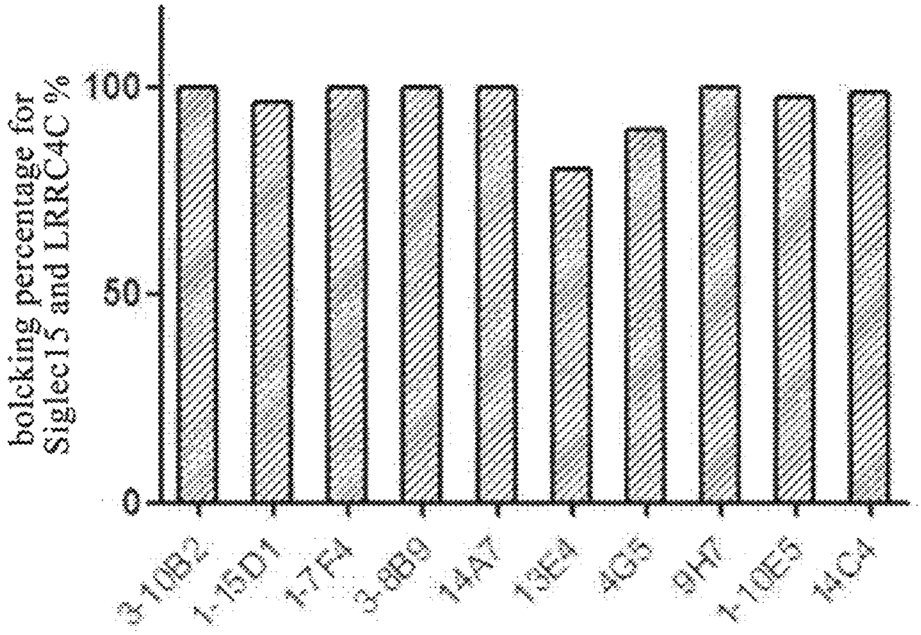
FIG. 2 shows the blocking effect of various exemplary anti-Siglec15 antibodies of the present application on the interaction between Siglec15 and LRRC4C-Hek293 cells.

When the hybridoma cells grew to a certain amount, the Siglec15-His protein was coated onto a 96-well microtiter plate, and the mouse anti-Siglec15 serum was used as a positive control, and the hybridoma supernatant was screened by ELISA to select positive clones. By detecting the supernatant of positive clones to block the binding of Siglec15-ECD-Fc to LRRC4C-Hek293 cells, it was found that 3-10B2, 1-15D1, 1-7F4, 3-8B9, 14A7, 13E4, 4G5, 9H7, 1-10E5 and 14C4 antibodies can block the binding of Siglec 15-ECD-Fc and LRRC4C-Hek293 cells. The experimental results were shown in FIG. 2, and the specific method was as follows. The inventors conducted subclonal screening of these 10 strains of cells by the limiting dilution method, and finally kept the obtained monoclonal positive cell strains separately, and the supernatant of hybridoma cells was collected for purification by ProteinG.

The specific method for single-point blocking flow cytometry detection of Siglec15-ECD-Fc binding to LRRC4C-Hek293 cells is as follows:

By using the Lipofectamine system, the human LRRC4C (amino acid sequence set forth in SEQ ID NO: 5) plasmid was transfected into Hek293 cells. After 48 hours, G418 (800 μg/mL) was added to screen for 10-14 days to obtain a cell line stably expressing LRRC4C. Cells were collected, washed once with PBS buffer, blocked with PBS containing 2% FBS for 1 h at room temperature. The hybridoma cell supernatant was added in 50 μl/well; then the diluted Siglec 15-ECD-Fc protein (2 μg/ml) was added in 50 μl/well; mouse IgG was used as a negative control. The cells were incubated at 4° C. for 50 min, then washed three times with PBS buffer containing 0.2% FBS, then diluted with Alexa Fluor 488-labeled goat anti-human IgG in PBS containing 2% FBS, and incubated at 4° C. in the dark for 50 min, and washed three times with PBS buffer containing 0.2% FBS; finally, the cells were resuspended in 200 μL PBS and analyzed by flow cytometry. The average fluorescence reading of 10,000 cells for each sample was recorded, wherein the FITC fluorescence intensity was taken as the abscissa and the cell number as the ordinate, and the voltage parameters were adjusted so that the blank control was at the origin of the coordinate axis. The percentage result of hybridoma cell supernatant for blocking the binding of Siglec15-ECD-Fc protein to LRRC4C was calculated. Blocking percentage %=(negative control reading value-test supernatant reading value-blank control reading value)/(negative control reading value-blank control reading).

The full-length amino acid sequence of human LRRC4C is as follows (SEQ ID NO: 5):

```
MLNKMTLHPQQIMIGPRFNRALFDPLLVVLLALQLLVVAGLVRAQTCPSV

CSCSNQFSKVICVRKNLREVPDGISTNTRLLNLHENQIQIIKVNSFKHLR

HLEILQLSRNHIRTIEIGAFNGLANLNTLELFDNRLTTIPNGAFVYLSKL

KELWLRNNPIESIPSYAFNRIPSLRRLDLGELKRLSYISEGAFEGLSNLR

YLNLAMCNLREIPNLTPLIKLDELDLSGNHLSAIRPGSFQGLMHLQKLWM

IQSQIQVIERNAFDNLQSLVEINLAHNNLTLLPHDLFTPLHHLERIHLHH

NPWNCNCDILWLSWWIKDMAPSNTACCARCNTPPNLKGRYIGELDQNYFT

CYAPVIVEPPADLNVTEGMAAELKCRASTSLTSVSWITPNGTVMTHGAYK

VRIAVLSDGTLNFTNVTVQDTGMYTCMVSNSVGNTTASATLNVTAATTTP

FSYFSTVTVETMEPSQDEARTTDNNVGPTPVVDWETTNVTTSLTPQSTRS

TEKTFTIPVTDINSGIPGIDEVMKTTKIIIGCFVAITLMAAVMLVIFYKM
```

-continued

```
RKQHHRQNHHAPTRTVEIINVDDEITGDTPMESHLPMPAIEHEHLNHYNS

YKSPFNHTTTVNTINSIHSSVHEPLLIRMNSKDNVQETQI
```

Example 5, Cross-Species Recognition Properties of Anti-Siglec15 Antibodies

Figure 3:
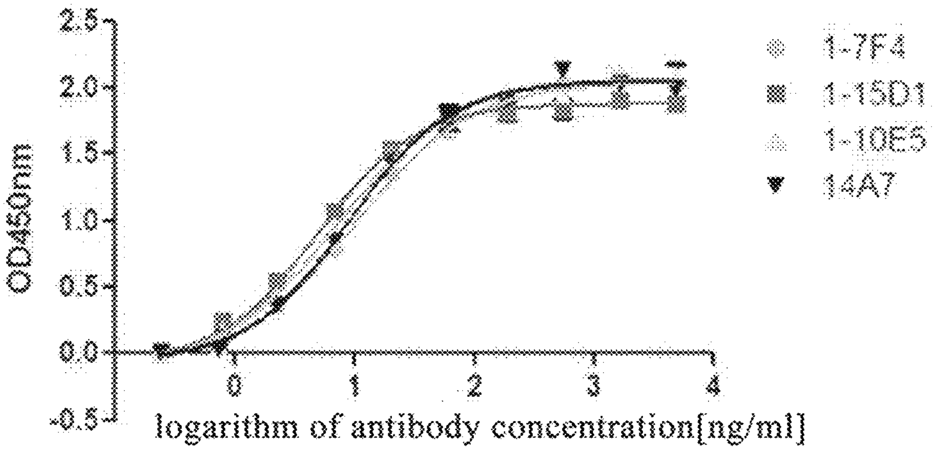
FIG. 3 shows the curves of ELISA detection results of various exemplary anti-Siglec15 antibodies of the present application binding to human Siglec15 protein.
Figure 4:
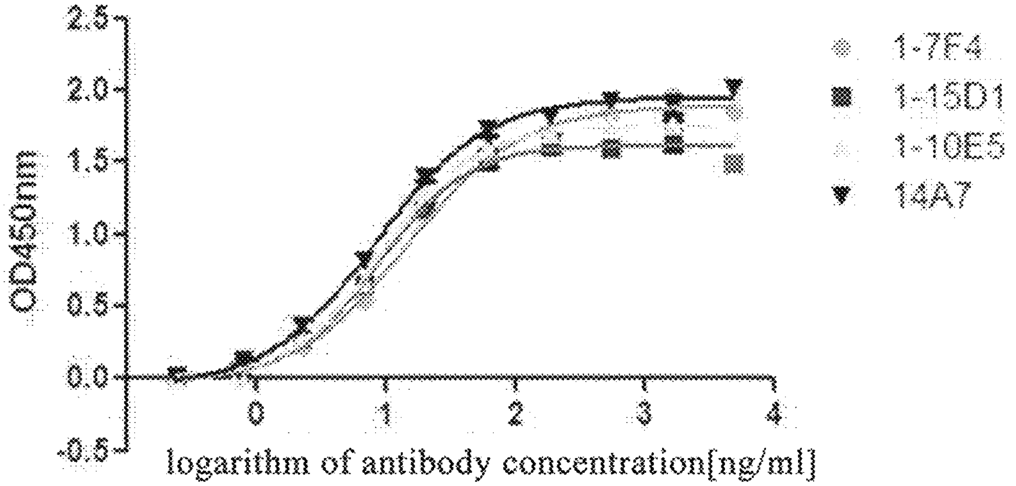
FIG. 4 shows the curves of ELISA detection results of various exemplary anti-Siglec15 antibodies of the present application binding to monkey Siglec15 protein.
Figure 5:
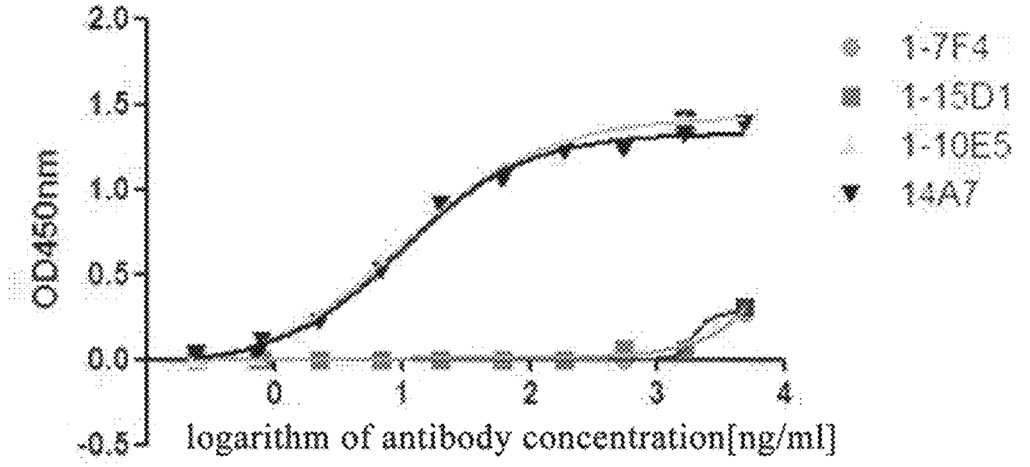
FIG. 5 shows the curves of ELISA detection results of various exemplary anti-Siglec 15 antibodies of the present application binding to mouse Siglec15 protein.

In order to evaluate the cross-species recognition properties of antibodies, the cross recognition of purified 1-15D1, 1-7F4, 14A7 and 1-10E5 monoclonal antibodies with human, cynomolgus monkey and mouse Siglec15 was tested. ELISA test was carried out by coating the microtiter plate with His-tagged human, cynomolgus monkey and mouse Siglec15 proteins and adding 1-15D1, 1-7F4, 14A7 and 1-10E5 antibodies at concentrations of 5000 ng/ml, 1666.7 ng/ml, 555.6 ng/ml, 185.2 ng/ml, 61.7 ng/ml, 20.6 ng/ml, 6.9 ng/ml, 2.3 ng/ml, 0.8 ng/ml, 0.25 ng/ml and 0.1 ng/ml respectively. The results showed that the 1-15D1, 1-7F4, 14A7 and 1-10E5 antibodies could bind to human (FIG. 3) and monkey (FIG. 4) Siglec15 proteins. The 14A7 and 1-10E5 antibodies could not only bind human and monkey Siglec15 proteins, but also bind mouse Siglec 15 proteins (FIG. 5). See Table 1 and FIG. 3-FIG. 5 for the $EC_{50}$ values of affinities for various Siglec15.

TABLE 1

$EC_{50}$ values of anti-Siglec15 antibodies binding to human, monkey and mouse Siglec15 proteins

| Name of antibody | $EC_{50}$ values for binding with Siglec15 protein (ng/ml) | | |
|---|---|---|---|
| | Human | Monkey | Mouse |
| 1-7F4 | 10.04 | 14.81 | NA |
| 1-15D1 | 4.98 | 9.075 | NA |
| 1-10E5 | 7.21 | 9.493 | 9.609 |
| 14A7 | 8.97 | 8.507 | 9.988 |

Example 6, Preparation, Expression and Purification of Human-Mouse Chimeric Anti-Siglec15 Antibodies Total RNA was extracted from $3\times10^6$ to $5\times10^6$ hybridoma cells using the Trizol method, and reverse-transcribed into cDNA according to the experimental guidelines of GoScript™ Reverse Transcription System. Murine immunoglobulin heavy and light chain variable region (V-region) fragments were subsequently amplified by PCR and sequenced. Finally, the sequences of the heavy chain and light chain CDR region (Table 2) and the amino acid sequences of the variable regions of clones 1-10E5, 1-7F4, 1-15D1 and 14A7 were obtained.

TABLE 2

CDR region sequences of antibody heavy chain variable region (VH) and light chain variable region (VL)

| Name of antibody | HCDR1 | HCDR2 | HCDR3 |
|---|---|---|---|
| 1-15D1 | TYVMH (SEQ ID NO: 6) | YINPYNDNTKYNEKFKG (SEQ ID NO: 7) | GYDAMDY (SEQ ID NO: 8) |

TABLE 2-continued

| CDR region sequences of antibody heavy chain variable region (VH) and light chain variable region (VL) | | | |
|---|---|---|---|
| 1-7F4 | TYVMH (SEQ ID NO: 6) | YINPYNDKTKYNEKFKG (SEQ ID NO: 12) | GYDAMDY (SEQ ID NO: 8) |
| 1-10E5 | RYTMS (SEQ ID NO: 14) | TISSGGNSTYYPDSVKG (SEQ ID NO: 15) | YGYFFDY (SEQ ID NO: 16) |
| 14A7 | SDFA (SEQ ID NO: 20) | YIRFSGSTTYKPTLKS (SEQ ID NO: 21) | EDYDGLFDY (SEQ ID NO: 22) |
| **Name of antibody** | **LCDR1** | **LCDR2** | **LCDR3** |
| 1-15D1 | RTSENIYSHLA (SEQ ID NO: 9) | SATNLAD (SEQ ID NO: 10) | QHFWGTPWT (SEQ ID NO: 11) |
| 1-7F4 | RASENIYSHLA (SEQ ID NO: 13) | SATNLAD (SEQ ID NO: 10) | QHFWGTPWT (SEQ ID NO: 11) |
| 1-10E5 | RASENIYSFLA (SEQ ID NO: 17) | NAKTLAE (SEQ ID NO: 18) | QHHYDRPLT (SEQ ID NO: 19) |
| 14A7 | RSSQTILHSNGNTYLD (SEQ ID NO: 23) | KVSNRFS (SEQ ID NO: 24) | FQGSHVPYT (SEQ ID NO: 25) |

The amino acid sequence of 1-15D1 heavy chain variable region (SEQ ID NO: 26)

EVQLQQSGPELVKPGASVKMSCKASGYTFTTYVMHWVKQKPGQGLEWIGY
INPYNDNTKYNEKFKGKATLTSDKSSSTAYMELSSLTSEDSAVYYCGSGY
DAMDYWGQGTSVTVSS

The amino acid sequence of 1-15D1 light chain variable region (SEQ ID NO: 27)

DIQMAQSPASLSVSVGETVTITCRTSENIYSHLAWYQQKQGKSPQLLVYS
ATNLADGVPSRFNGSGSGTQYSLKINSLQSEDFGSYYCQHFWGTPWTFGG
GTKLEIK

The amino acid sequence of 1-7F4 heavy chain variable region (SEQ ID NO: 28)

EVQLQQSGPELVKPGASVKMSCKASGYTFTTYVMHWVKQKPGQGLEWIGY
INPYNDKTKYNEKFKGKATLTSDKSSSTAYMEVSRLTSEDSAVYYCGSGY
DAMDYWGQGTSVTVSS

The amino acid sequence of 1-7F4 light chain variable region (SEQ ID NO: 29)

DIQMTQSPASLSVSVGETVTITCRASENIYSHLAWYQQKQGKSPQLLIYS
ATNLADGVPSRFNGSGSGTQYSLKINSLQSEDFGSYYCQHFWGTPWTFGG
GTKLEIK

The amino acid sequence of 1-10E5 heavy chain variable region (SEQ ID NO: 30)

DVKLVESGGGLVKPGGSLKLSCVVSGLTFSRYTMSWVRQTPEKRLEWVAT
ISSGGNSTYYPDSVKGRFTISRDDAKDTLYLQMSSLKSEDTAMYYCTNYG
YFFDYWGQGTTLTVSS

The amino acid sequence of 1-10E5 light chain variable region (SEQ ID NO: 31)

DIQMTQSPASLSASVGETVTITCRASENIYSFLAWYQQKQGKSPQLLVYN
AKTLAEGVPSRFSGSGSGTQFSLKINSLQPEDFGSYYCQHHYDRPLTFGA
GTKLELK

The amino acid sequence of 14A7 heavy chain variable region (SEQ ID NO: 32)

DVQLQESGPGLVKPSQSLSLTCTVTGYSITSDFAWNWIRQFPGNKLEWMG
YIRFSGSTTYKPTLKSRISITRDTSKNQFFLQLNSVTTEDSATYYCARED
YDGLFDYWGQGTTLTVTS

The amino acid sequence of 14A7 light chain variable region (SEQ ID NO: 33)

DVLMTQTPLSLPVSLGDHASISCRSSQTILHSNGNTYLDWYLQKPGQSPK
LLIYKVSNRFSGVPDRFSGSGSGTDFTLKISRVEAEDLGVYYCFQGSHVP
YTFGGGTKLEIK

According to the variable region sequence information of the above four monoclonal antibody coding genes, a human-mouse chimeric antibody expression vector was constructed. The antibody subtype was human IgG1, in which asparagine (N) at position 297 was mutated to alanine (A) (abbreviated as hIgG1 in the application). DNA fragments comprising light chain variable region and constant region (Kappa) and heavy chain variable region and constant region were synthesized respectively, and inserted into pCDNA3.1 expression vector respectively to form expression plasmids. The obtained eukaryotic expression vector was transiently transformed into Hek293 cells and cultured for 5 to 7 days. The cell supernatant was collected by centrifugation, and the harvested culture supernatant was purified through a ProteinA column to obtain the target antibodies, which were named 1-7F4-IgG1, 1-15D1-IgG1, 1-10E5-IgG1 and 14A7-IgG1.

Example 7, ForteBio Determination of the Affinity of Chimeric Antibody and Siglec15 Protein The control antibody selected in this example was the antibody 5G12 in Chinese Patent Application Publication CN110035769A. The CDR region sequence was from CN110035769A. As shown in Example 6, it was connected to hIgG1 (containing N297A mutation) to prepare 5G12-IgG1. The control antibody 5G12 was the anti-Siglec 15 drug antibody NC-318 from NextCure Company that the inventor analyzed and deduced.

In this experiment, a HIS1K biosensor was used to bind the ligand (Sigle15-ECD-His protein) followed by the analyte. Human Sigle15-ECD-His protein was diluted to 5

μg/ml and immobilized on the biosensor to a binding response threshold of 0.3 nm. After the 120s baseline step, the sensors were respectively immersed in the analytes of anti-Siglec15 antibodies 1-7F4-IgG1, 1-15D1-IgG1 and 1-10E5-IgG1 diluted in 2-fold gradient dilution with 0.02% PBST buffer, and the initial antibody concentration was 100 nM, 7 concentration gradients were set respectively. Human IgG1 (hIgG1) (B109801, Baiying Biotechnology Co., Ltd.) was used as a reference control, and 5G12-IgG1 was used as a positive control to conduct an affinity analysis experiment. The binding time of ligand and analyte was 120s, and the dissociation time was 300s. The raw data were imported into the analysis software, the zero concentration control was subtracted, and the reference channel was subtracted to eliminate the volume effect. The affinity data of the antigen and antibody were calculated by the analysis software regression according to the binding curve. The results were shown in Table 3. The candidate antibody could recognize the target antigen with high affinity, and the KD values were significantly lower than those of the control antibody 5G12.

TABLE 3

The binding affinity of anti-Siglec15 chimeric antibody to human Siglec15 protein detected by Fortebio

| Name of antibody | Ka(1/Ms) | Kd(1/s) | KD(M) |
|---|---|---|---|
| 1-7F4-IgG1 | 5.7E5 | 3.42E−5 | 6E−11 |
| 1-10E5-IgG1 | 1.04E6 | <1E−7 | <1E−12 |
| 1-15D1-IgG1 | 4.36E5 | <1E−7 | <1E−12 |
| 5G12-IgG1 | 6.83E5 | 1.78E−4 | 2.61E−10 |

Example 8, Binding Properties of Anti-Siglec15 Chimeric Antibody to Hek293 Cell Line Expressing Siglec15

Figure 6:
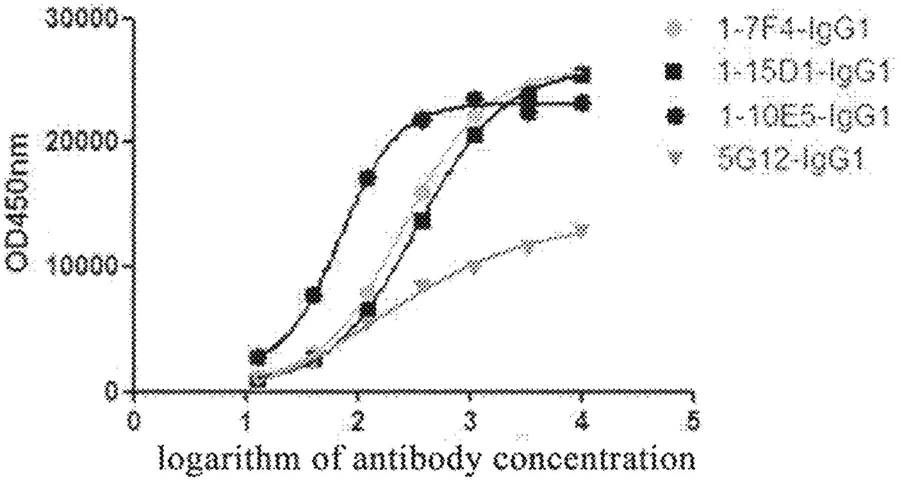
FIG. 6 shows the binding result curves of various exemplary anti-Siglec15 chimeric antibodies of the present application and control antibodies to Hek293 cells expressing human Siglec15.

The Hek293 cell line overexpressing human Siglec15 was used to evaluate the binding ability of anti-Siglec15 chimeric antibody to human Siglec15 expressed on the cell surface. The human-mouse chimeric antibody was diluted with PBS buffer to concentrations of 10000 ng/ml, 5000 ng/ml, 1666.7 ng/ml, 555.6 ng/ml.2, 61.7 ng/ml and 20.6 ng/ml, and 5G12-IgG1 was used as a positive control. The antibody was incubated with Hek293-siglec15 cells at 4° C. for 1 h. The cells were washed three times with PBS buffer, and then labeled with Alexa Fluor488-labeled goat anti-human IgG antibody on ice for 50 min in the dark. The cells were washed three times with PBS buffer, and the fluorescence intensity of the cells was read by flow cytometry. As shown in FIG. 6, the 1-10E5-IgG1, 1-7F4-IgG1, and 1-15D1-IgG1 antibodies could dose-dependently bind Siglec 15 expressed on the Hek293 cell line, and the binding strength was significantly higher than that of the control antibody 5G12.

Example 9, Anti-Siglec15 Antibody could Reverse Siglec15-Mediated Inhibition of T Cell Proliferation The inventors tested the reversal of Siglec 15-mediated inhibition of human whole PBMC T cell proliferation by recombinant chimeric antibodies. On the day of the assay, frozen PBMCs were thawed, washed with RPMI complete medium and counted. PMBCs ($3\times10^5$ cells/well) were seeded in 96-well plates containing anti-human CD3 antibody (OKT3, 50 ng/ml; eBioScience) in advance. Then, the pre-mixed Siglec15-ECD-Fc fusion protein (5 μg/ml) and the antibody to be tested (20 μg/ml) were added to the designated wells. The hIgG1 was used as a negative control (Isotype), and 5G12-IgG1 was used as a positive control. After the cells were cultured at 37° C. for 72 h, CellTiter-Glo (Promega) was added to detect cell viability.

Figure 7:
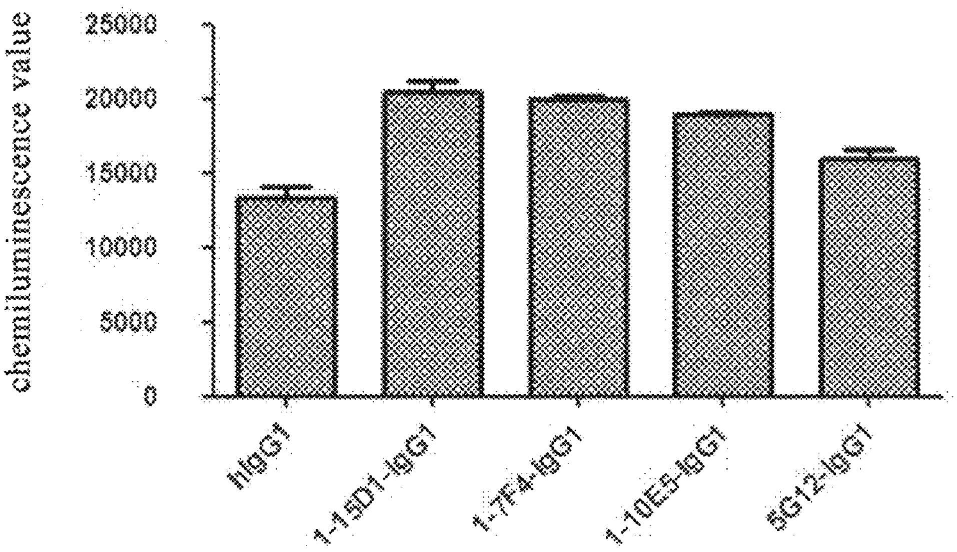
FIG. 7 shows a diagram showing the effect of various exemplary anti-Siglec15 chimeric antibodies of the present application and control antibodies on reversing the inhibition of the proliferation of PBMC lymphocytes by Siglec15 protein.

As shown in FIG. 7, compared with the negative control antibody hIgG1, 1-15D1-IgG1, 1-7F4-IgG1 and 1-10E5-IgG1 recombinant antibodies could reverse Siglec15-mediated inhibition of human T cells, and the effects were better than those of the control antibody 5G12.

Example 10, Anti-Siglec15 Antibody could Reverse Siglec15-Mediated Inhibition of T Cell Secretion of IFN-γ

In this experiment, the activation effect of PBMC was evaluated by detecting the amount of IFN-γ secreted by human-derived PBMC through an in vitro immunostimulation experiment, so as to characterize the activity of anti-Siglec-15 antibody. PBMCs were isolated from peripheral blood of pooled healthy people, washed with RPMI complete medium and counted. Whole PMBCs ($3\times10^5$ cells/well) were seeded in 96-well plates containing anti-human CD3 antibody (OKT3, 50 ng/ml; eBioScience) in advance. Then, the pre-mixed Siglec 15-ECD-Fc fusion protein (5 μg/ml) and the antibody to be tested at a concentration of 20 μg/ml were added to the designated wells. The hIgG1 was used as a negative control (Isotype), and 5G12-IgG1 was used as a positive control. After the cells were cultured at 37° C. for 24 h, the supernatant was collected by centrifugation to detect the release of IFN-γ.

Figure 8:
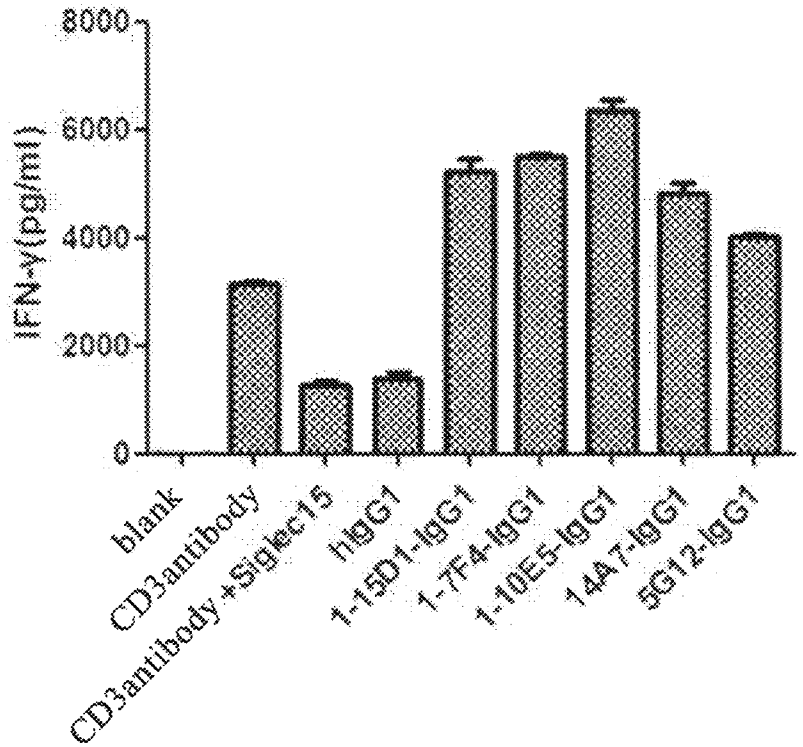
FIG. 8 shows a diagram showing the effect of various exemplary anti-Siglec15 chimeric antibodies of the present application and control antibodies on reversing the inhibition of IFN-γ secretion of PBMC lymphocytes by Siglec15 protein.

As shown in FIG. 8, 1-15D1-IgG1, 1-7F4-IgG1 and 1-10E5-IgG1 recombinant antibodies could effectively reverse Siglec15-mediated inhibition of T cell secretion of IFN-γ, and the effects were significantly better than those of the control antibody 5G12.

Example 11, Epitope Classification of Anti-Siglec15 Antibodies

The epitope classification of 1-15D1-IgG1, 1-7F4-IgG1, 1-10E5-IgG1 and 5G12-IgG1 was detected by Octet epitope pairing. The human Siglec15-ECD-His protein was loaded on the HIS1K sensor at 5 μg/ml, and then exposed to the primary antibody and the secondary antibody respectively. Whether the two antibodies recognize the same epitope was determined by the binding signal of the secondary antibody, and the data was processed using ForteBio's data analysis software 7.0. Additional binding (60%-100%) of the secondary antibody after primary antibody association indicated an unoccupied epitope (non-competition); additional partial binding (10%-60%) of the secondary antibody after primary antibody association indicated a partially occupied epitope (partial competition); and no binding (less than 10%) indicated epitope blocking (competition). Results showed that the recognition epitopes of 1-7F4-IgG1 and 1-15D1-IgG1 were the same, and the recognition epitopes of 1-10E5-IgG1 and 1-7F4-IgG1 and 1-15D1-IgG1 partially overlapped; the recognition epitopes of 1-10E5-IgG1, 1-7F4-IgG1 and 1-15D1-IgG1 were completely different from those of 5G12-IgG1.

The above descriptions are only exemplary embodiments, which are only examples and do not limit the combination of features necessary to implement the application. The headings provided are not meant to limit the various embodiments of the application. Terms such as "comprising", "including", and "containing" are not intended to be limiting. In addition, unless otherwise stated, the absence of a numerical modifier includes the plural, and “or” means “and/or”. Unless otherwise defined herein, all technical and scientific terms used herein have the same meaning as commonly understood by one of ordinary skill in the art. All publications and patents mentioned in this application are incorporated herein by reference. Various modifications and variations of the described methods and compositions of the application will be apparent to those skilled in the art without departing from the scope and spirit of the application. Although the application has been described in terms of specific preferred embodiments, it should be understood that the application as claimed should not be unduly limited to such specific embodiments. Indeed, various modifications of the described modes for carrying out the application which are obvious to those skilled in the relevant fields are intended to be within the scope of the following claims.

The invention claimed is:

1. An anti-Siglec15 antibody or antigen-binding fragment thereof comprising a heavy chain variable region and a light chain variable region, wherein the heavy chain variable region comprises a heavy chain complementarity-determining region (HCDR) 1, an HCDR2, and an HCDR3, and the light chain variable region comprises a light chain complementarity-determining region (LCDR) 1, an LCDR2, and an LCDR3, wherein:

the heavy chain variable region comprises HCDR1 having the amino acid sequence set forth in SEQ ID NO: 6, HCDR2 having the amino acid sequence set forth in SEQ ID NO: 7, and HCDR3 having the amino acid sequence set forth in SEQ ID NO: 8, and the light chain variable region comprises LCDR1 having the amino acid sequence set forth in SEQ ID NO: 9, LCDR2 having the amino acid sequence set forth in SEQ ID NO: 10, and LCDR3 having the amino acid sequence set forth in SEQ ID NO: 11; or the heavy chain variable region comprises HCDR1 having the amino acid sequence set forth in SEQ ID NO: 6, HCDR2 having the amino acid sequence set forth in SEQ ID NO: 12, and HCDR3 having the amino acid sequence set forth in SEQ ID NO: 8, and the light chain variable region comprises LCDR1 having the amino acid sequence set forth in SEQ ID NO: 13, LCDR2 having the amino acid sequence set forth in SEQ ID NO: 10, and LCDR3 having the amino acid sequence set forth in SEQ ID NO: 11; or the heavy chain variable region comprises HCDR1 having the amino acid sequence set forth in SEQ ID NO: 14, HCDR2 having the amino acid sequence set forth in SEQ ID NO: 15, and HCDR3 having the amino acid sequence set forth in SEQ ID NO: 16, and the light chain variable region comprises LCDR1 having the amino acid sequence set forth in SEQ ID NO: 17, LCDR2 having the amino acid sequence set forth in SEQ ID NO: 18, and LCDR3 having the amino acid sequence set forth in SEQ ID NO: 19; or the heavy chain variable region comprises HCDR1 having the amino acid sequence set forth in SEQ ID NO: 20, HCDR2 having the amino acid sequence set forth in SEQ ID NO: 21, and HCDR3 having the amino acid sequence set forth in SEQ ID NO: 22, and the light chain variable region comprises LCDR1 having the amino acid sequence set forth in SEQ ID NO: 23, LCDR2 having the amino acid sequence set forth in SEQ ID NO: 24, and LCDR3 having the amino acid sequence set forth in SEQ ID NO: 25, wherein the amino acid sequences of HCDR1, HCDR2, HCDR3, LCDR1, LCDR2, and LCDR3 are defined according to Kabat.

2. The anti-Siglec15 antibody or antigen-binding fragment thereof according to claim 1, wherein the heavy chain variable region has the amino acid sequence set forth in SEQ ID NO: 26, 28, 30 or 32, or an amino acid sequence having at least 80%, at least 90%, at least 95%, or at least 99% homology with the amino acid sequence set forth in SEQ ID NO: 26, 28, 30 or 32.

3. The anti-Siglec15 antibody or antigen-binding fragment thereof according to claim 1, wherein the light chain variable region has the amino acid sequence set forth in SEQ ID NO: 27, 29, 31 or 33, or an amino acid sequence having at least 80%, at least 90%, at least 95%, or at least 99% homology with the amino acid sequence set forth in SEQ ID NO: 27, 29, 31 or 33.

4. The anti-Siglec15 antibody or antigen-binding fragment thereof according to claim 1, wherein:

the heavy chain variable region has the amino acid sequence set forth in SEQ ID NO: 26, or an amino acid sequence having at least 80%, at least 90%, at least 95%, or at least 99% homology with the amino acid sequence set forth in SEQ ID NO: 26, and the light chain variable region has the amino acid sequence set forth in SEQ ID NO: 27, or an amino acid sequence having at least 80%, at least 90%, at least 95%, or at least 99% homology with the amino acid sequence set forth in SEQ ID NO: 27;

or the heavy chain variable region has the amino acid sequence set forth in SEQ ID NO: 28, or an amino acid sequence having at least 80%, at least 90%, at least 95%, or at least 99% homology with the amino acid sequence set forth in SEQ ID NO: 28, and the light chain variable region has the amino acid sequence set forth in SEQ ID NO: 29, or an amino acid sequence having at least 80%, at least 90%, at least 95%, or at least 99% homology with the amino acid sequence set forth in SEQ ID NO: 29;

or the heavy chain variable region has the amino acid sequence set forth in SEQ ID NO: 30, or an amino acid sequence having at least 80%, at least 90%, at least 95%, or at least 99% homology with the amino acid sequence set forth in SEQ ID NO: 30, and the light chain variable region has the amino acid sequence set forth in SEQ ID NO: 31, or an amino acid sequence having at least 80%, at least 90%, at least 95%, or at least 99% homology with the amino acid sequence set forth in SEQ ID NO: 31;

or the heavy chain variable region has the amino acid sequence set forth in SEQ ID NO: 32, or an amino acid sequence having at least 80%, at least 90%, at least 95%, or at least 99% homology with the amino acid sequence set forth in SEQ ID NO: 32, and the light chain variable region has the amino acid sequence set forth in SEQ ID NO: 33, or an amino acid sequence having at least 80%, at least 90%, at least 95%, or at least 99% homology with the amino acid sequence set forth in SEQ ID NO: 33.

5. The anti-Siglec15 antibody or antigen-binding fragment thereof according to claim 1, wherein:

the anti-Siglec15 antibody is a complete antibody, a single-chain antibody (scFv) or a bispecific antibody; and/or the antigen-binding fragment is Fab, Fab', Fv or $F(ab')_2$; and/or the anti-Siglec15 antibody is a murine antibody, a chimeric antibody, a humanized antibody or a human antibody; and/or the anti-Siglec15 antibody is a monoclonal antibody; and/or the anti-Siglec15 antibody is IgG1, IgG2 or IgG4 isotype; and/or the anti-Siglec15 antibody comprises a kappa or lambda subtype of light chain constant region.

6. A pharmaceutical composition comprising the anti-Siglec15 antibody or antigen-binding fragment thereof according to claim 1, and a pharmaceutically acceptable excipient, diluent agent or carrier.

7. An immunoconjugate comprising the anti-Siglec15 antibody or antigen-binding fragment thereof according to claim 1 conjugated to a therapeutic agent.

8. The immunoconjugate according to claim 7, wherein the therapeutic agent is an antitumor drug.

9. A method for inhibiting growth of tumor cells that express Siglec15 or treating a hyperproliferative disease characterized by Siglec15 expression in an individual in need thereof, comprising administering to the individual a therapeutically effective amount of the anti-Siglec15 antibody or antigen-binding fragment thereof according to claim 1.

10. The method according to claim 9, wherein the hyperproliferative disease is a tumor that expresses Siglec15.

11. The method according to claim 9, further comprising administering an anti-PD-1 antibody or anti-PD-L1 antibody to the individual.

12. An isolated polynucleotide encoding the anti-Siglec15 antibody or antigen-binding fragment according to claim 1.

13. A vector comprising a polynucleotide encoding the anti-Siglec15 antibody or antigen-binding fragment according to claim 1.

14. An isolated host cell comprising the vector according to claim 13.

15. A method for preparing the anti-Siglec15 antibody or antigen-binding fragment thereof according to claim 1, comprising a step of culturing the host cell according to claim 14; optionally, the method further comprises a step of isolating the anti-Siglec15 antibody or antigen-binding fragment thereof.

* * * * *

```
                              SEQUENCE LISTING

<160> NUMBER OF SEQ ID NOS: 33

<210> SEQ ID NO 1
<211> LENGTH: 328
<212> TYPE: PRT
<213> ORGANISM: Homo sapiens

<400> SEQUENCE: 1

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Ala Ser Thr Val Ala Leu Leu Leu Gly Ala Leu Gly
            260                 265                 270

Phe Lys Ala Leu Leu Leu Leu Gly Val Leu Ala Ala Arg Ala Ala Arg
        275                 280                 285

Arg Arg Pro Glu His Leu Asp Thr Pro Asp Thr Pro Pro Arg Ser Gln
    290                 295                 300
```

```
Ala Gln Glu Ser Asn Tyr Glu Asn Leu Ser Gln Met Asn Pro Arg Ser
305                 310                 315                 320

Pro Pro Ala Thr Met Cys Ser Pro
                325


<210> SEQ ID NO 2
<211> LENGTH: 494
<212> TYPE: PRT
<213> ORGANISM: Artificial Sequence
<220> FEATURE:
<223> OTHER INFORMATION: The amino acid sequence of Siglec15-ECD-Fc

<400> SEQUENCE: 2

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Ala Ser Thr Pro Lys Ser Cys Asp Lys Thr His Thr
            260                 265                 270

Cys Pro Pro Cys Pro Ala Pro Glu Leu Leu Gly Gly Pro Ser Val Phe
        275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335
```

-continued

```
Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys
                485                 490


<210> SEQ ID NO 3
<211> LENGTH: 396
<212> TYPE: PRT
<213> ORGANISM: Artificial Sequence
<220> FEATURE:
<223> OTHER INFORMATION: The amino acid sequence of Siglec15-IgV-Fc

<400> SEQUENCE: 3

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Pro Lys Ser Cys Asp Lys Thr His Thr Cys Pro
                165                 170                 175

Pro Cys Pro Ala Pro Glu Leu Leu Gly Gly Pro Ser Val Phe Leu Phe
            180                 185                 190

Pro Pro Lys Pro Lys Asp Thr Leu Met Ile Ser Arg Thr Pro Glu Val
        195                 200                 205
```

```
Thr Cys Val Val Val Asp Val Ser His Glu Asp Pro Glu Val Lys Phe
    210                 215                 220

Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
            260                 265                 270

Ser Asn Lys Ala Leu Pro Ala Pro Ile Glu Lys Thr Ile Ser Lys Ala
        275                 280                 285

Lys Gly Gln Pro Arg Glu Pro Gln Val Tyr Thr Leu Pro Pro Ser Arg
    290                 295                 300

Asp Glu Leu Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
            340                 345                 350

Phe Phe Leu Tyr Ser Lys Leu Thr Val Asp Lys Ser Arg Trp Gln Gln
        355                 360                 365

Gly Asn Val Phe Ser Cys Ser Val Met His Glu Ala Leu His Asn His
    370                 375                 380

Tyr Thr Gln Lys Ser Leu Ser Leu Ser Pro Gly Lys
385                 390                 395


<210> SEQ ID NO 4
<211> LENGTH: 270
<212> TYPE: PRT
<213> ORGANISM: Artificial Sequence
<220> FEATURE:
<223> OTHER INFORMATION: The amino acid sequence of Siglec15-ECD-His

<400> SEQUENCE: 4

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175
```

```
Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Ala Ser Thr His His His His His His His
            260                 265                 270


<210> SEQ ID NO 5
<211> LENGTH: 640
<212> TYPE: PRT
<213> ORGANISM: Homo sapiens

<400> SEQUENCE: 5

Met Leu Asn Lys Met Thr Leu His Pro Gln Gln Ile Met Ile Gly Pro
1               5                   10                  15

Arg Phe Asn Arg Ala Leu Phe Asp Pro Leu Leu Val Val Leu Leu Ala
            20                  25                  30

Leu Gln Leu Leu Val Val Ala Gly Leu Val Arg Ala Gln Thr Cys Pro
        35                  40                  45

Ser Val Cys Ser Cys Ser Asn Gln Phe Ser Lys Val Ile Cys Val Arg
    50                  55                  60

Lys Asn Leu Arg Glu Val Pro Asp Gly Ile Ser Thr Asn Thr Arg Leu
65                  70                  75                  80

Leu Asn Leu His Glu Asn Gln Ile Gln Ile Ile Lys Val Asn Ser Phe
                85                  90                  95

Lys His Leu Arg His Leu Glu Ile Leu Gln Leu Ser Arg Asn His Ile
            100                 105                 110

Arg Thr Ile Glu Ile Gly Ala Phe Asn Gly Leu Ala Asn Leu Asn Thr
        115                 120                 125

Leu Glu Leu Phe Asp Asn Arg Leu Thr Thr Ile Pro Asn Gly Ala Phe
    130                 135                 140

Val Tyr Leu Ser Lys Leu Lys Glu Leu Trp Leu Arg Asn Asn Pro Ile
145                 150                 155                 160

Glu Ser Ile Pro Ser Tyr Ala Phe Asn Arg Ile Pro Ser Leu Arg Arg
                165                 170                 175

Leu Asp Leu Gly Glu Leu Lys Arg Leu Ser Tyr Ile Ser Glu Gly Ala
            180                 185                 190

Phe Glu Gly Leu Ser Asn Leu Arg Tyr Leu Asn Leu Ala Met Cys Asn
        195                 200                 205

Leu Arg Glu Ile Pro Asn Leu Thr Pro Leu Ile Lys Leu Asp Glu Leu
    210                 215                 220

Asp Leu Ser Gly Asn His Leu Ser Ala Ile Arg Pro Gly Ser Phe Gln
225                 230                 235                 240

Gly Leu Met His Leu Gln Lys Leu Trp Met Ile Gln Ser Gln Ile Gln
                245                 250                 255

Val Ile Glu Arg Asn Ala Phe Asp Asn Leu Gln Ser Leu Val Glu Ile
            260                 265                 270

Asn Leu Ala His Asn Asn Leu Thr Leu Leu Pro His Asp Leu Phe Thr
        275                 280                 285
```

Pro Leu His His Leu Glu Arg Ile His Leu His His Asn Pro Trp Asn
    290                 295                 300

Cys Asn Cys Asp Ile Leu Trp Leu Ser Trp Trp Ile Lys Asp Met Ala
305                 310                 315                 320

Pro Ser Asn Thr Ala Cys Cys Ala Arg Cys Asn Thr Pro Pro Asn Leu
                325                 330                 335

Lys Gly Arg Tyr Ile Gly Glu Leu Asp Gln Asn Tyr Phe Thr Cys Tyr
            340                 345                 350

Ala Pro Val Ile Val Glu Pro Pro Ala Asp Leu Asn Val Thr Glu Gly
        355                 360                 365

Met Ala Ala Glu Leu Lys Cys Arg Ala Ser Thr Ser Leu Thr Ser Val
    370                 375                 380

Ser Trp Ile Thr Pro Asn Gly Thr Val Met Thr His Gly Ala Tyr Lys
385                 390                 395                 400

Val Arg Ile Ala Val Leu Ser Asp Gly Thr Leu Asn Phe Thr Asn Val
                405                 410                 415

Thr Val Gln Asp Thr Gly Met Tyr Thr Cys Met Val Ser Asn Ser Val
            420                 425                 430

Gly Asn Thr Thr Ala Ser Ala Thr Leu Asn Val Thr Ala Ala Thr Thr
        435                 440                 445

Thr Pro Phe Ser Tyr Phe Ser Thr Val Thr Val Glu Thr Met Glu Pro
    450                 455                 460

Ser Gln Asp Glu Ala Arg Thr Thr Asp Asn Asn Val Gly Pro Thr Pro
465                 470                 475                 480

Val Val Asp Trp Glu Thr Thr Asn Val Thr Thr Ser Leu Thr Pro Gln
                485                 490                 495

Ser Thr Arg Ser Thr Glu Lys Thr Phe Thr Ile Pro Val Thr Asp Ile
            500                 505                 510

Asn Ser Gly Ile Pro Gly Ile Asp Glu Val Met Lys Thr Thr Lys Ile
        515                 520                 525

Ile Ile Gly Cys Phe Val Ala Ile Thr Leu Met Ala Ala Val Met Leu
    530                 535                 540

Val Ile Phe Tyr Lys Met Arg Lys Gln His His Arg Gln Asn His His
545                 550                 555                 560

Ala Pro Thr Arg Thr Val Glu Ile Ile Asn Val Asp Asp Glu Ile Thr
                565                 570                 575

Gly Asp Thr Pro Met Glu Ser His Leu Pro Met Pro Ala Ile Glu His
            580                 585                 590

Glu His Leu Asn His Tyr Asn Ser Tyr Lys Ser Pro Phe Asn His Thr
        595                 600                 605

Thr Thr Val Asn Thr Ile Asn Ser Ile His Ser Ser Val His Glu Pro
    610                 615                 620

Leu Leu Ile Arg Met Asn Ser Lys Asp Asn Val Gln Glu Thr Gln Ile
625                 630                 635                 640

<210> SEQ ID NO 6
<211> LENGTH: 5
<212> TYPE: PRT
<213> ORGANISM: Artificial Sequence
<220> FEATURE:
<223> OTHER INFORMATION: 1-15D1 HCDR1

<400> SEQUENCE: 6

Thr Tyr Val Met His
1               5

<210> SEQ ID NO 7
<211> LENGTH: 17
<212> TYPE: PRT
<213> ORGANISM: Artificial Sequence
<220> FEATURE:
<223> OTHER INFORMATION: 1-15D1 HCDR2

<400> SEQUENCE: 7

```
Tyr Ile Asn Pro Tyr Asn Asp Asn Thr Lys Tyr Asn Glu Lys Phe Lys
1               5                   10                  15

Gly
```

<210> SEQ ID NO 8
<211> LENGTH: 7
<212> TYPE: PRT
<213> ORGANISM: Artificial Sequence
<220> FEATURE:
<223> OTHER INFORMATION: 1-15D1 HCDR3

<400> SEQUENCE: 8

```
Gly Tyr Asp Ala Met Asp Tyr
1               5
```

<210> SEQ ID NO 9
<211> LENGTH: 11
<212> TYPE: PRT
<213> ORGANISM: Artificial Sequence
<220> FEATURE:
<223> OTHER INFORMATION: 1-15D1 LCDR1

<400> SEQUENCE: 9

```
Arg Thr Ser Glu Asn Ile Tyr Ser His Leu Ala
1               5                   10
```

<210> SEQ ID NO 10
<211> LENGTH: 7
<212> TYPE: PRT
<213> ORGANISM: Artificial Sequence
<220> FEATURE:
<223> OTHER INFORMATION: 1-15D1 LCDR2

<400> SEQUENCE: 10

```
Ser Ala Thr Asn Leu Ala Asp
1               5
```

<210> SEQ ID NO 11
<211> LENGTH: 9
<212> TYPE: PRT
<213> ORGANISM: Artificial Sequence
<220> FEATURE:
<223> OTHER INFORMATION: 1-15D1 LCDR3

<400> SEQUENCE: 11

```
Gln His Phe Trp Gly Thr Pro Trp Thr
1               5
```

<210> SEQ ID NO 12
<211> LENGTH: 17
<212> TYPE: PRT
<213> ORGANISM: Artificial Sequence
<220> FEATURE:
<223> OTHER INFORMATION: 1-7F4 HCDR2

<400> SEQUENCE: 12

```
Tyr Ile Asn Pro Tyr Asn Asp Lys Thr Lys Tyr Asn Glu Lys Phe Lys
```

1 5 10 15

Gly

<210> SEQ ID NO 13
<211> LENGTH: 11
<212> TYPE: PRT
<213> ORGANISM: Artificial Sequence
<220> FEATURE:
<223> OTHER INFORMATION: 1-7F4 LCDR1

<400> SEQUENCE: 13

Arg Ala Ser Glu Asn Ile Tyr Ser His Leu Ala
1 5 10

<210> SEQ ID NO 14
<211> LENGTH: 5
<212> TYPE: PRT
<213> ORGANISM: Artificial Sequence
<220> FEATURE:
<223> OTHER INFORMATION: 1-10E5 HCDR1

<400> SEQUENCE: 14

Arg Tyr Thr Met Ser
1 5

<210> SEQ ID NO 15
<211> LENGTH: 17
<212> TYPE: PRT
<213> ORGANISM: Artificial Sequence
<220> FEATURE:
<223> OTHER INFORMATION: 1-10E5 HCDR2

<400> SEQUENCE: 15

Thr Ile Ser Ser Gly Gly Asn Ser Thr Tyr Tyr Pro Asp Ser Val Lys
1 5 10 15

Gly

<210> SEQ ID NO 16
<211> LENGTH: 7
<212> TYPE: PRT
<213> ORGANISM: Artificial Sequence
<220> FEATURE:
<223> OTHER INFORMATION: 1-10E5 HCDR3

<400> SEQUENCE: 16

Tyr Gly Tyr Phe Phe Asp Tyr
1 5

<210> SEQ ID NO 17
<211> LENGTH: 11
<212> TYPE: PRT
<213> ORGANISM: Artificial Sequence
<220> FEATURE:
<223> OTHER INFORMATION: 1-10E5 LCDR1

<400> SEQUENCE: 17

Arg Ala Ser Glu Asn Ile Tyr Ser Phe Leu Ala
1 5 10

<210> SEQ ID NO 18
<211> LENGTH: 7
<212> TYPE: PRT
<213> ORGANISM: Artificial Sequence
<220> FEATURE:
<223> OTHER INFORMATION: 1-10E5 LCDR2

<400> SEQUENCE: 18

Asn Ala Lys Thr Leu Ala Glu
1 5

<210> SEQ ID NO 19
<211> LENGTH: 9
<212> TYPE: PRT
<213> ORGANISM: Artificial Sequence
<220> FEATURE:
<223> OTHER INFORMATION: 1-10E5 LCDR3

<400> SEQUENCE: 19

Gln His His Tyr Asp Arg Pro Leu Thr
1 5

<210> SEQ ID NO 20
<211> LENGTH: 4
<212> TYPE: PRT
<213> ORGANISM: Artificial Sequence
<220> FEATURE:
<223> OTHER INFORMATION: 14A7 HCDR1

<400> SEQUENCE: 20

Ser Asp Phe Ala
1

<210> SEQ ID NO 21
<211> LENGTH: 16
<212> TYPE: PRT
<213> ORGANISM: Artificial Sequence
<220> FEATURE:
<223> OTHER INFORMATION: 14A7 HCDR2

<400> SEQUENCE: 21

Tyr Ile Arg Phe Ser Gly Ser Thr Thr Tyr Lys Pro Thr Leu Lys Ser
1 5 10 15

<210> SEQ ID NO 22
<211> LENGTH: 9
<212> TYPE: PRT
<213> ORGANISM: Artificial Sequence
<220> FEATURE:
<223> OTHER INFORMATION: 14A7 HCDR3

<400> SEQUENCE: 22

Glu Asp Tyr Asp Gly Leu Phe Asp Tyr
1 5

<210> SEQ ID NO 23
<211> LENGTH: 16
<212> TYPE: PRT
<213> ORGANISM: Artificial Sequence
<220> FEATURE:
<223> OTHER INFORMATION: 14A7 LCDR1

<400> SEQUENCE: 23

Arg Ser Ser Gln Thr Ile Leu His Ser Asn Gly Asn Thr Tyr Leu Asp
1 5 10 15

<210> SEQ ID NO 24
<211> LENGTH: 7
<212> TYPE: PRT
<213> ORGANISM: Artificial Sequence
<220> FEATURE:
<223> OTHER INFORMATION: 14A7 LCDR2

<400> SEQUENCE: 24

```
Lys Val Ser Asn Arg Phe Ser
1               5


<210> SEQ ID NO 25
<211> LENGTH: 9
<212> TYPE: PRT
<213> ORGANISM: Artificial Sequence
<220> FEATURE:
<223> OTHER INFORMATION: 14A7 LCDR3

<400> SEQUENCE: 25

Phe Gln Gly Ser His Val Pro Tyr Thr
1               5


<210> SEQ ID NO 26
<211> LENGTH: 116
<212> TYPE: PRT
<213> ORGANISM: Artificial Sequence
<220> FEATURE:
<223> OTHER INFORMATION: The amino acid sequence of 1-15D1 heavy chain
      variable region

<400> SEQUENCE: 26

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Thr Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Asn Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Gly Ser Gly Tyr Asp Ala Met Asp Tyr Trp Gly Gln Gly Thr Ser Val
            100                 105                 110

Thr Val Ser Ser
        115


<210> SEQ ID NO 27
<211> LENGTH: 107
<212> TYPE: PRT
<213> ORGANISM: Artificial Sequence
<220> FEATURE:
<223> OTHER INFORMATION: The amino acid sequence of 1-15D1 light chain
      variable region

<400> SEQUENCE: 27

Asp Ile Gln Met Ala Gln Ser Pro Ala Ser Leu Ser Val Ser Val Gly
1               5                   10                  15

Glu Thr Val Thr Ile Thr Cys Arg Thr Ser Glu Asn Ile Tyr Ser His
            20                  25                  30

Leu Ala Trp Tyr Gln Gln Lys Gln Gly Lys Ser Pro Gln Leu Leu Val
        35                  40                  45

Tyr Ser Ala Thr Asn Leu Ala Asp Gly Val Pro Ser Arg Phe Asn Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
```

```
                85                  90                  95

Thr Phe Gly Gly Gly Thr Lys Leu Glu Ile Lys
            100                 105


<210> SEQ ID NO 28
<211> LENGTH: 116
<212> TYPE: PRT
<213> ORGANISM: Artificial Sequence
<220> FEATURE:
<223> OTHER INFORMATION: The amino acid sequence of 1-7F4 heavy chain
      variable region

<400> SEQUENCE: 28

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Thr Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Lys Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Val Ser Arg Leu Thr Ser Glu Asp Ser Ala Val Tyr Tyr Cys
                85                  90                  95

Gly Ser Gly Tyr Asp Ala Met Asp Tyr Trp Gly Gln Gly Thr Ser Val
            100                 105                 110

Thr Val Ser Ser
        115


<210> SEQ ID NO 29
<211> LENGTH: 107
<212> TYPE: PRT
<213> ORGANISM: Artificial Sequence
<220> FEATURE:
<223> OTHER INFORMATION: The amino acid sequence of 1-7F4 light chain
      variable region

<400> SEQUENCE: 29

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser His
            20                  25                  30

Leu Ala Trp Tyr Gln Gln Lys Gln Gly Lys Ser Pro Gln Leu Leu Ile
        35                  40                  45

Tyr Ser Ala Thr Asn Leu Ala Asp Gly Val Pro Ser Arg Phe Asn Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys
            100                 105


<210> SEQ ID NO 30
<211> LENGTH: 116
<212> TYPE: PRT
<213> ORGANISM: Artificial Sequence
<220> FEATURE:
<223> OTHER INFORMATION: The amino acid sequence of 1-10E5 heavy chain
```

variable region

<400> SEQUENCE: 30

Asp Val Lys Leu Val Glu Ser Gly Gly Gly Leu Val Lys Pro Gly Gly
1 5 10 15

Ser Leu Lys Leu Ser Cys Val Val Ser Gly Leu Thr Phe Ser Arg Tyr
20 25 30

Thr Met Ser Trp Val Arg Gln Thr Pro Glu Lys Arg Leu Glu Trp Val
35 40 45

Ala Thr Ile Ser Ser Gly Gly Asn Ser Thr Tyr Tyr Pro Asp Ser Val
50 55 60

Lys Gly Arg Phe Thr Ile Ser Arg Asp Asp Ala Lys Asp Thr Leu Tyr
65 70 75 80

Leu Gln Met Ser Ser Leu Lys Ser Glu Asp Thr Ala Met Tyr Tyr Cys
85 90 95

Thr Asn Tyr Gly Tyr Phe Phe Asp Tyr Trp Gly Gln Gly Thr Thr Leu
100 105 110

Thr Val Ser Ser
115

<210> SEQ ID NO 31
<211> LENGTH: 107
<212> TYPE: PRT
<213> ORGANISM: Artificial Sequence
<220> FEATURE:
<223> OTHER INFORMATION: The amino acid sequence of 1-10E5 light chain
variable region

<400> SEQUENCE: 31

Asp Ile Gln Met Thr Gln Ser Pro Ala Ser Leu Ser Ala Ser Val Gly
1 5 10 15

Glu Thr Val Thr Ile Thr Cys Arg Ala Ser Glu Asn Ile Tyr Ser Phe
20 25 30

Leu Ala Trp Tyr Gln Gln Lys Gln Gly Lys Ser Pro Gln Leu Leu Val
35 40 45

Tyr Asn Ala Lys Thr Leu Ala Glu Gly Val Pro Ser Arg Phe Ser Gly
50 55 60

Ser Gly Ser Gly Thr Gln Phe Ser Leu Lys Ile Asn Ser Leu Gln Pro
65 70 75 80

Glu Asp Phe Gly Ser Tyr Tyr Cys Gln His His Tyr Asp Arg Pro Leu
85 90 95

Thr Phe Gly Ala Gly Thr Lys Leu Glu Leu Lys
100 105

<210> SEQ ID NO 32
<211> LENGTH: 118
<212> TYPE: PRT
<213> ORGANISM: Artificial Sequence
<220> FEATURE:
<223> OTHER INFORMATION: The amino acid sequence of 14A7 heavy chain
variable region

<400> SEQUENCE: 32

Asp Val Gln Leu Gln Glu Ser Gly Pro Gly Leu Val Lys Pro Ser Gln
1 5 10 15

Ser Leu Ser Leu Thr Cys Thr Val Thr Gly Tyr Ser Ile Thr Ser Asp
20 25 30

Phe Ala Trp Asn Trp Ile Arg Gln Phe Pro Gly Asn Lys Leu Glu Trp
35 40 45

-continued

```
Met Gly Tyr Ile Arg Phe Ser Gly Ser Thr Thr Tyr Lys Pro Thr Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Ser Ala Thr Tyr Tyr Cys
                85                  90                  95

Ala Arg Glu Asp Tyr Asp Gly Leu Phe Asp Tyr Trp Gly Gln Gly Thr
            100                 105                 110

Thr Leu Thr Val Thr Ser
        115


<210> SEQ ID NO 33
<211> LENGTH: 112
<212> TYPE: PRT
<213> ORGANISM: Artificial Sequence
<220> FEATURE:
<223> OTHER INFORMATION: The amino acid sequence of 14A7 light chain
      variable region

<400> SEQUENCE: 33

Asp Val Leu Met Thr Gln Thr Pro Leu Ser Leu Pro Val Ser Leu Gly
1               5                   10                  15

Asp His Ala Ser Ile Ser Cys Arg Ser Ser Gln Thr Ile Leu His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```